(12) United States Patent
Steinmetz et al.

(10) Patent No.: US 12,359,175 B2
(45) Date of Patent: Jul. 15, 2025

(54) VIRAL NANOPARTICLE MULTIMERS

(71) Applicant: CASE WESTERN RESERVE UNIVERSITY, Cleveland, OH (US)

(72) Inventors: Nicole F. Steinmetz, Cleveland, OH (US); Amy M. Wen, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 691 days.

(21) Appl. No.: 17/544,518

(22) Filed: Dec. 7, 2021

(65) Prior Publication Data
US 2022/0090026 A1   Mar. 24, 2022

Related U.S. Application Data

(63) Continuation of application No. 14/761,444, filed as application No. PCT/US2013/077924 on Dec. 27, 2013, now Pat. No. 11,193,111.

(60) Provisional application No. 61/753,558, filed on Jan. 17, 2013.

(51) Int. Cl.
*C12N 7/00* (2006.01)
*C07K 14/005* (2006.01)
*B82Y 5/00* (2011.01)

(52) U.S. Cl.
CPC .............. *C12N 7/00* (2013.01); *C07K 14/005* (2013.01); *B82Y 5/00* (2013.01); *C12N 2770/32023* (2013.01); *C12N 2770/32051* (2013.01); *C12N 2770/32142* (2013.01); *C12N 2810/856* (2013.01)

(58) Field of Classification Search
None
See application file for complete search history.

(56) References Cited

U.S. PATENT DOCUMENTS

| | | |
|---|---|---|
| 5,004,606 A | 4/1991 | Frincke |
| 5,342,770 A | 8/1994 | Yamasaki |
| 5,736,146 A | 4/1998 | Cohen et al. |
| 7,569,340 B2 | 8/2009 | Mirkin et al. |
| 7,820,426 B2 | 10/2010 | Wang et al. |
| 9,925,281 B2 | 3/2018 | Steinmetz et al. |
| 10,086,095 B2 | 10/2018 | Steinmetz et al. |
| 10,207,014 B2 | 2/2019 | Steinmetz et al. |
| 10,478,510 B2 | 11/2019 | Steinmetz |
| 11,020,497 B2 | 6/2021 | Steinmetz et al. |
| 11,167,047 B2 | 11/2021 | Steinmetz et al. |
| 11,253,610 B2 | 2/2022 | Steinmetz |
| 2005/0019270 A1 | 1/2005 | Finlay et al. |
| 2007/0248617 A1 | 10/2007 | Bachmann et al. |
| 2007/0258889 A1 | 11/2007 | Douglas et al. |
| 2007/0284545 A1 | 12/2007 | Isacsson et al. |
| 2008/0124358 A1 | 5/2008 | Brennan |
| 2009/0280188 A1 | 11/2009 | Mirkin et al. |
| 2010/0183504 A1 | 7/2010 | Chen |
| 2012/0015899 A1* | 1/2012 | Lomonossoff ........ A61P 35/00 435/254.2 |
| 2020/0179468 A1 | 6/2020 | Steinmetz |
| 2022/0211881 A1 | 7/2022 | Steinmetz |

FOREIGN PATENT DOCUMENTS

| | | |
|---|---|---|
| JP | 2009524699 A | 7/2009 |
| WO | 1997014443 A1 | 4/1997 |
| WO | 01/18199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |
| WO | 2015/0039255 A1 | 3/2015 |
| WO | 2015/188110 A1 | 12/2015 |
| WO | 2016073972 A1 | 5/2016 |
| WO | 2016/149264 A1 | 9/2016 |
| WO | 2017/004123 A1 | 1/2017 |

OTHER PUBLICATIONS

Filpula D, Zhao H. Releasable PEGylation of proteins with customized linkers. Adv Drug Deliv Rev. Jan. 3, 2008;60(1):29-49. (Year: 2008).*
Steinmetz NF, Lin T, Lomonossoff GP, Johnson JE. Structure-based engineering of an icosahedral virus for nanomedicine and nanotechnology. Curr Top Microbiol Immunol. 2009;327:23-58. (Year: 2009).*
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).
Le, Duc et al. Chemical addressability of potoato virus X for its applications in bio/nanotechnology. El Sevier. Journal of Structural Biology 200 (2017). pp. 360-368. (Year: 2017).
Czapar, Anna et al. Tobacco Mosaic Virus Delivery of Phenanthriplatin for Cancer therapy. American Chemical Society. Nano 2016 (10) pp. 4119-4126 (Year: 2016).

(Continued)

*Primary Examiner* — Shanon A. Foley
(74) *Attorney, Agent, or Firm* — Tarolli, Sundheim, Covell & Tummino LLP

(57) ABSTRACT

Virus particle multimers and methods of making and using such virus particle multimer are described. Virus particle multimers are constructed by preparing a plurality of asymmetrically functionalized virus particles bearing one or more functional groups and contacting the asymmetrically functionalized virus particles with a first linker molecule that reacts with the functional groups to form a virus particle multimer that includes a plurality of asymmetrically functionalized virus particles connected by the linker molecule. The asymmetrically functionalized virus particles are typically prepared by attaching the virus particles to a support surface to allow asymmetrical functionalization to be introduced.

19 Claims, 5 Drawing Sheets

(56) References Cited

OTHER PUBLICATIONS

Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Nicole F. Steinmetz, U.S. Appl. No. 16/998,210, filed Aug. 7, 2020; Non-Final OA dated Dec. 7, 2022.
Pretto et al. ("Versatile reversible cross-linking strategy to stabilize CCMV virus like particles for efficient siRNA delivery." Bioconjugate chemistry 30.12 (2019): 3069-3077).
Mosquera et al. (Acc. Chem. Res. 2018, 51, 9, 2305-2313 Publication Date: Aug. 29, 2018.
Imamura et al. ("FOXA 1 promotes tumor progression in prostate cancer via the insulin-like growth factor binding protein 3 pathway." (2012).
Lam, et al. (WIREs Nanomed Nanobiotechnol Jan./Feb. 2018 vol. 10: 1-18).
Nicole F.Steinmetz; U.S. Appl. No. 16/759,652, filed Apr. 27, 2020; Final Office Action, dated Dec. 12, 2022; 15 pgs.
Nicole F.Steinmetz; U.S. Appl. No. 17/129,463, filed Dec. 21, 2020; Non-Final Office Action, dated Dec. 8, 2022; 32 pgs.
Nicole F.Steinmetz; U.S. Appl. No. 16/597,509, filed Oct. 9, 2019; Non-Final Office Action, dated Dec. 27, 2022; 12 pgs.
Mitoxantrone. Drug Bank Online. Website. https://go.drugbank.com/drugs/DB01204. (Accessed Dec. 15, 2022) (Year: 2022).
Tamoxifen. Drug Bank Online. Website. https://go.drugbank.com/drugs/DB00675. (Accessed: Dec. 15, 2022) (Year: 2022).
Xiao et al. (International Journal of Molecular Medicine. 2016; 38: 1319-326).
Zhang et al. (Theranostics. 2018; 8 (9): 2521-2548).
Pellico et al. (Contrast Media and Molecular Imaging. 2019; Article ID 1845637: 1-13).
Bruckman et al. (Nano Letters. Mar. 2014; 14: 1551-1558).
Royston et al. (Journal of Colloidal and Interface Science. 2009; 332: 402-407).
Nicole F.Steinmetz; U.S. Appl. No. 17/522,182, filed Nov. 9, 2021; Non-Final Office Action, dated Jan. 5, 2023; 27 pgs.
Temming et al. (bioconjugate Chemistry. 2006; 17: 1385-1394).
Nicole F.Steinmetz; U.S. Appl. No. 17/677,147, filed Feb. 22, 2022; Non-Final Office Action, dated Jan. 13, 2023; 22 pgs.
Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.
Applicant: Case Western Reserve University; "Cancer Immunotherapy Using Virus Particles"; European Patent Application No. 21201960.8; Extended European Search Report dated Jan. 19, 2022; 11 pgs.
Brennan, et al., "Cowpea Mosaic Virus as a Vaccine Carrier of Heterologous Antigens", Molecular Biotechnology, vol. 17, No. 1, Jan. 2001.
Gonzalez, et al., "Interaction of Cowpea Mosaic Virus (CPMV) Nanoparticles with Antigen Presenting Cells in Vitro and In Vivo", PLOS ONE, vol. 4, No. 11, Nov. 2009.
Patrick h. Iizotte: "Novel approaches to targeting innate immunity for cancer Immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders Ket al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Lin et al. The Refined Crystal Structure of Cowpea Mosaic Virus at 2.8 A Resolution. Virology 265, 20±34 (1999) (Year: 1999).
Wang et al. Icosahedral Virus Particles as Addressable Nanoscale Building Blocks. Angew. Chem. Int. Ed. 2002; 41(3): 459-462.
Barnhill et al. Turnip Yellow Mosaic Virus as a Chemoaddressable Bionanoparticle. Bioconj. Chem. 2007; 18(852-859).
He et al. "Self-Assembly of Tobacco Mosaic Virus at Oil/Water Interfaces", Langmuir, 2009; 25(9): 4979-4987.
Chapter 7: Multifuntional Cross-Linking Reagents (pp. 239-264) in Chemistry of Protein and Nucleic Acid Cross-linking and Conjugation: Second Edition, Shan S. Wong and David M. Jameson Editors Published Oct. 10, 2011 by CRC Press Reference.
Kaur et al. Crosslinking of viral nanoparticles with "clickable" fluorescent crosslinkers at the interface. Sci. China: Chem. 201 0; 53(6): 1287-1293.
Lee et al. Viruses and Virus-Like Protein Assemblies—Chemically Programmable Nanoscale Building Blocks. Nano Res. 2009; 2: 349-3654.
Pokorski and Steinmetz (The art of engineering viral nanoparticles. Mol. Pharmaceut. 201 O; 8(1 ): 29-43.
Abul Kashem, Mottakin M., et al. "Two-and Three-Dimensional Network of Nanoparticles via Polymer-Mediated Self-Assembly " ACS Macro Letters 1.3 (2012): 396-399.
Janat-Amsbury, M. M., et al. "Geometry and surface characteristics of gold nanoparticles influence their biodistribution and uptake by macrophages." European Journal of Pharmaceutics and Biopharmaceutics 77.3 (2011 ): 417-423.
Barua, Sutapa, et al. "Particle shape enhances specificity of antibody-displaying nanoparticles." Proceedings of the National Academy of Sciences 110.9 (2013): 3270-3275.
Boturyn, Didier, et al. "Template assembled cyclopeptides as multimeric system for integrin targeting and endocytosis." Journal of the American Chemical Society 126.18 (2004): 5730-5739.
Chen, Ying, et al. "Shape controlled growth of gold nanoparticles by a solution synthesis." Chem. Commun. 33 (2005): 4181-4183.
Dai, Qiu, et al. "A "nanonecklace" synthesized from monofunctionalized gold nanoparticles." Journal of the American Chemical Society 127.22 (2005): 8008-8009.
Dam, Duncan Hieu M., et al. "Direct observation of nanoparticle-cancer cell nucleus interactions." ACS nano 6.4 (2012): 3318-3326.
Decuzzi, P., et al. "Size and shape effects in the biodistribution of intravascularly injected particles." Journal of Controlled Release 141.3 (2010): 320-327.
Desgrosellier, Jay S., and David A. Cheresh. "Integrins in cancer: biological implications and therapeutic opportunities." Nature Reviews Cancer 10.1 (2010): 9-22.
Frankamp, Benjamin L., Andrew K. Boal, and Vincent M. Rotello. "Controlled interparticle spacing through self-assembly of Au nanoparticles and poly (amidoamine) dendrimers." Journal of the American Chemical Society 124.51 ? (2002): 15146-1514 7.
Gao, Huajian, Wendong Shi, and Lambert B. Freund. "Mechanics of receptor-mediated endocytosis." Proceedings of the National Academy of Sciences of the United States of America 102.27 (2005): 9469-94 74.
Gratton, Stephanie EA, et al. "The effect of particle design on cellular internalization pathways." Proceedings of the National Academy of Sciences 105.33 (2008): 11613-11618.
Hillaireau, Herve, and Patrick Couvreur. "Nanocarriers' entry into the cell: relevance to drug delivery." Cellular and Molecular Life Sciences 66.17 (2009): 2873-2896.
Jeong, Sangmoo, et al. "Fast and scalable printing of large area monolayer nanoparticles for nanotexturing applications." Nano letters 10.8 (2010): 2989-2994.

(56) References Cited

OTHER PUBLICATIONS

Jiang, Wen, et al. "Nanoparticle-mediated cellular response is size-dependent." Nature nanotechnology 3.3 (2008): 145-150.
Kim, Do Youb, et al. "Synthesis of Gold Nano-hexapods with Controllable Arm Lengths and Their Tunable Optical Properties." Angewandte Chemie 123.28 (2011 ): 6452-6455.
Klem, Michael T., et al. "2-D array formation of genetically engineered viral cages on Au surfaces and imaging by atomic force microscopy." Journal of the American Chemical Society 125.36 (2003): 10806-10807.
Konjevi6, G., V. Jurisi6, and I. Spuzi6. "Corrections to the original lactate dehydrogenase (LOH) release assay for the evaluation of NK cell cytotoxicity." Journal of immunological methods 200.1 (1997): 199-201.
Li, Tao, et al. "Core/shell biocomposites from the hierarchical assembly of bionanoparticles and polymer." Small 4.1 0 (2008): 1624-1629.
Park, Ji-Ho, et al. "Magnetic iron oxide nanoworms for tumor targeting and imaging." Advanced Materials 20.9 (2008): 1630-1635.
Peiris, Pubudu M., et al. "Assembly of linear nano-chains from iron oxide nanospheres with asymmetric surface chemistry." PloS one 6.1 (2011): e15927.
Schaeublin, Nicole M., et al. "Does shape matter? Bioeffects of gold nanomaterials in a human skin cell model." Langmuir 28.6 (2012): 3248-3258.
Steinmetz, Nicole F., David J. Evans, and George P. Lomonossoff. "Chemical introduction of reactive thiols into a viral hanoscaffold: a method that avoids virus aggregation." ChemBioChem 8.10 (2007): 1131-1136.
Tietze, Lutz F., et al. "Conjugation of p-aminophenyl glycosides with squaric acid diester to a carrier protein and the use of the neoglycoprotein in the histochemical detection of lectins." Bioconjugate chemistry 2.3 (1991): 148-153.
Wen, Amy M., et al. "Interior engineering of a viral nanoparticle and its tumor homing properties." Biomacromolecules 13.12 (2012): 3990-4001.
Wen, Amy M., et al. "Design rules for nanomedical engineering: from physical virology to the applications of virus-based materials in medicine." Journal of biological physics 39.2 (2013): 301-325.
Brunel et al., "A Hydrazone Ligation Strategy to Assemble Multifunctional Viral Nanoparticles for Cell Imaging and Tumor Targeting", Nano Lett., Mar. 10, 2010, 10(3), pp. 1093-1097.
Cheng et al., "Fungal Virus Capsids, Cytoplasmic Compartments for the Replicatino of Double Stranded RNA, Formed as Icosahedral Shells of Asymmetric Gag Dimers", J. Mol. Biol., 1994, 244, pp. 255-258.
Lee et al., "Viruses and Virus-Like Protein Assemblies—Chemically Programmable Nanoscale Building Blocks", Nano Res., 2009, 2, pp. 349-364.
Suci et al., "A Streptavidin—Protein Cage Janus Particle for Polarized Targeting and Modular Functionalization", J. Am. Chem. Soc., 2009, 131, pp. 9164-9165.
International Search Report and Written Opinion for PCT/US13/77924, mailed Mar. 19, 2014, pp. 1-2.
"CWRU researcher to turn plant virus shells against human cancers", The Daily, CWRU Researcher to Turn Plant Virus Shells Against Human Cancers. Case Western Reserve University, Apr. 18, 2016.
Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
Wen et al. Design of virus-based nanomaterials for medicine, biotechnology, and energy. Chem. Soc. Rev., 2016, 45, 4074. DOI: 10.1039/c5cs00287g (Year: 2016).

Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).
Office action for Japanese Patent Application No. 2017-524349, drafted Jan. 31, 2020; Mailed Feb. 10, 2020; 6 pgs.
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Sheen et al., "Stimulating Antitumor Immunity with Nanoparticles", Wiley Interdiscip Rev Nanomed Nanobiotechnol, Oct. 2014, vol. 6, pp. 496-505.
Office action for Chinese Patent Application No. 201580063662.6, dated Mar. 4, 2020.
Office action for European Patent Application No. 15 857 504.3-1111, dated Mar. 18, 2020.
Mldiz, et al., "Applications of viral nanoparticles in medicine", Current Opinion in Biotechnology, vol. 22, Issue 6, (2011); pp. 901-908.
European Search Report for Patent Application No. 15857504.3-1111/3215520, dated May 7, 2018.
International Search Report for Application No. PCT/US15/59675 (2016).
Smyth et al. Treatment of rapidly growing K-BALB and CT26 mouse tumours using Semliki Forest virus and its derived vector. Gene Therapy (2005) 12, 147-159.
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Applicant: Case Western Reserve University; "Cancer Immunotherapy Using Virus Particles"; Canadian Office Action, dated Aug. 4, 2020; 3 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
Lizotte, et al., "Plant-derived viral-like nanoparticle immunotherapy suppress development of metastatic lung cancer", Journal of Immunology, vol. 194, Issue 1 Supplement, May 2015; 4 pgs.
Plchova et al. Expression of Human papillomavirus 16 E7ggg oncoprotein on N- and C-terminus of Potato virus X coat protein in bacterial and plant cells. Protein Expression and Purification 77 (2011); p. 146-152.

* cited by examiner

Fig. 1

VIRAL NANOPARTICLE MULTIMERS

CROSS-REFERENCE TO RELATED APPLICATIONS

This application claims priority to U.S. Provisional Patent Application Ser. No. 61/753,558, filed Jan. 17, 2013, which is incorporated herein by reference

GOVERNMENT FUNDING

The present invention was supported by National Science Foundation grant CMMI NM 333651 and National Institutes of Health grant NIBIB R00 EB009105. The Government has certain rights in this invention.

BACKGROUND

Particles at the nanoscale are becoming increasingly attractive in a wide array of applications, including electronics, sensing, and medicine. Due to their size and quantum effects, nanoparticles exhibit unique chemical, magnetic, electronic, and optical properties. Nanoparticles can be made from a diverse range of organic and inorganic materials, and they can be assembled into interesting hierarchical architectures to impart them with additional properties. Examples of such structures include nanohexapods (Kim et al., Angew. Chem., Int. Ed., 50 (28), 6328-6331 (2011)) nanostars (Dam et al., ACS Nano 6 (4), 3318-3326 (2012)), octahedrons (Chen et al., Chem. Commun. (Camb) (33), 4181-4183 (2005)), and nanoworms (Park et al., Adv. Mater. 20 (9), 1630-1635 (2008). The capacity for sizing and shaping of nanostructured features with temporal and spatial control is key for producing the next generation of higher-performing products with diverse applications and implications for future nanoelectronic and nanomedical devices.

A technological hurdle to mesoscale nanostructured materials is the availability of high-precision manufacturing technologies that facilitate large-scale robust assembly while simultaneously providing spatial control at the nanometer level. Top-down approaches enabled through lithographic techniques have progressed to provide tight control of feature dimensions and impeccable reproducibility. Rolland et al., J. Am. Chem. Soc., 127 (28), 10096-10100 (2005). However, while impressive in their implementation, the technology is highly specialized, with fundamental limitations around a few tens of nanometers for high throughput production. On the other hand, bottom-up approaches are in a way mimicking what nature has achieved, as biological systems and cells are self-assembled from the bottom up and, as systems, orchestrate complex functionalities.

Current techniques for bottom-up assembled nanoparticle architectures have led to the development of ID nanoworms/chains (Peiris et al., PLoS One, 6 (1), e15927 (2011)), 2D monolayers (Jeong et al., Nano Lett., 10 (8), 2989-2994 (2010); Abul Kashem et al., ACS Macro Lett., 1, 396-399 (2012)), and 3D clusters (Li et al., Small, 4 (10), 1624-1629 (2008); Frankamp et al., J. Am. Chem. Soc., 124 (51), 15146-15147 (2002)). There has been some preliminary work to expand on this toolbox through the decoration of long polylysine chains with small 2 nm gold particles to form nanonecklaces. Dai et al., J. Am. Chem. Soc., 127 (22), 8008-8009 (2005) However, there was high variability in product formation, and the distribution of products was unclear. In addition, there remain other highly relevant designs that require greater control of the three-dimensional arrangement of nanoparticles, which is not yet achievable. 3D directional bonding and assembly was only just recently demonstrated on a much larger size scale using polystyrene microparticles, but the method presented involved highly specialized chemistry which may be difficult to translate to other types of particles. Wang et al., Nature, 491 (7422), 51-55 (2012).

To date most bottom-up self-assembly approaches have focused on the assembly of symmetrical nanomaterials. Although symmetry provides a high degree of multivalency, symmetry also limits the possibilities in which higher-order hierarchical structures could be constructed. One application for a collection of symmetrical nanomaterials is in nanomedicine, the branch of science and engineering focused on the study and application of delivery systems for therapy and imaging. A challenge remains to understand the rules for the design of clinically effective delivery systems. Nanoparticle assemblies of varying size and aspect ratio provide a tool to elucidate the optimal in vivo characteristics (margination, circulation time, clearance, etc.) for the design of the best delivery system with enhanced efficacy or sensitivity. Decuzzi et al., J. Controlled Release, 141 (3), 320-327 (2010); Wen et al., J. Biol. Phys., DOI:10.1007/s10867-10013-19314-z (2013).

While the development pipeline for nanoparticle platform technologies continues to move rapidly, the fundamental nanomaterial-cell interactions have been studied only in a limited way. Size, shape, composition and surface chemistry of the nanocarrier impacts its biodistribution, cell interaction, and intracellular trafficking. Some fundamentals are understood. Mammalian cell membranes are negatively charged, therefore positively charged nanomaterials interact more strongly compared to negatively charged counterparts. Arnida et al., Eur. J. Pharm. Biopharm., 77 (3), 417-423 (2011) PEGylation can be used to camouflage nanoparticles and inhibit (or reduce) cell uptake; and receptor targeting is an effective strategy to enhance cell binding and/or induce tissue specificity. Hillaireau, H.; Couvreur, P., Cell. Mol. Life Sci., 66 (17), 2873-2896 (2009) Nevertheless, other data remain elusive, especially with regard to understanding how non-spherical nanomaterials interact with cells. For instance, in terms of aspect ratio (AR), some data indicate that higher AR materials have enhanced cellular interaction properties (Gratton et al., Proc. Natl. Acad. Sci. U.S.A., 105 (33), 11613-11618 (2008)), while other data indicate the opposite. Schaeublin et al., Langmuir, 28 (6), 3248-3258 (2012). Aside from differences in experimental setup between studies, a crucial drawback that affects the ability to interpret these data and conclusively determine shape-based effects is varying surface properties of the nanoparticles being compared; for example, the zeta potential of gold rods differ significantly from spheres, measuring +17 to +24 mV and −38 to −18 mV, respectively. It is clear that there is a critical need for a method that eliminates surface charge and other confounding variables in order to fully understand how parameters such as size, shape, and flexibility affect cellular interactions.

SUMMARY

The inventors describe herein a novel method for the production of nanoparticle clusters and chains of varying aspect ratio. In contrast to previous investigations of nanomaterial interactions, the various assemblies obtained using our presented method are composed of identical particles, thus keeping charge and surface properties consistent. Also provided are novel insights into the unique behaviors that can be discovered through comparison of various assemblies. The inventors explored the application of symmetry-breaking of nanoparticles to provide a higher degree of freedom and spatial control in the way that individual nanostructures can be interconnected into a mesoscale assembly. The inventors demonstrate a highly versatile approach that is modular in nature and can be used with a wide selection of nanoparticles. By combining symmetry breaking of nanoparticles and reacting with various polymers containing the appropriate functionality, an array of nanoparticle assemblies can be developed.

In particular, the inventors focused on comparing the different iterations of dimers that can be generated. Multifunctional assemblies were formed where targeting molecules (specifically cyclic RGD peptides that target integrins overexpressed on cancer cells) and fluorescent dyes (for optical imaging) were either homogeneously displayed throughout the dimer or concentrated on just a single nanoparticle component; these assemblies were compared to untargeted variations as well as single particles. The cell uptake properties of these homo- and heterodimers were evaluated, with clear effects found resulting from shape as well as spatial organization of the targeting molecules. The experiments illustrate how the assembly techniques described have significant implications as a novel approach to understanding the influences of various design parameters.

BRIEF DESCRIPTION OF THE FIGURES

The present invention may be more readily understood by reference to the following drawings.

FIG. 1 provides a scheme showing symmetry-breaking of CPMV using solid-state support approaches. a) Method 1: thiols are first introduced, CPMV bound to the support, then free thiols passivated. b) Method 2: CPMV bound to support using linker with disulfide bond then released.

DETAILED DESCRIPTION

Figure 2:
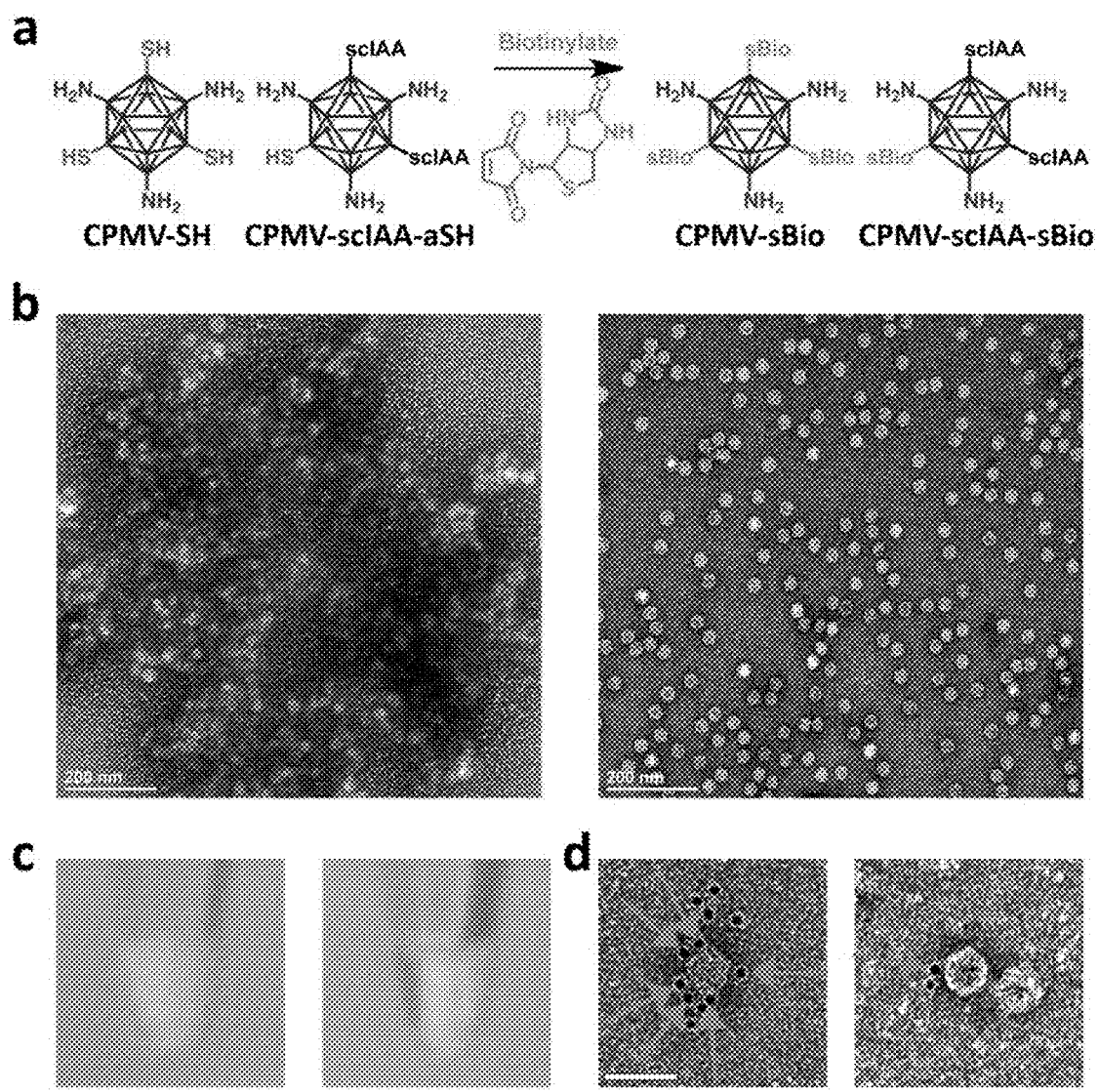
FIG. 2 provides graphs and images showing the characterization of symmetry-broken particles. a) Biotinylation of symmetric CPMV-SH and asymmetric CPMV-scIAA-aSH particles. b) TEM images show introduction of avidin causes aggregation of CPMV-sBio (left) but not CPMV-scIAA-sBio (right). c) Visual inspection of the samples also reveals aggregation for CPMV-sBio+avidin (left), while CPMV-scIAA-sBio+avidin (right) remains clear. d) Immunogold staining using gold-labeled anti-biotin of CPMV-sBio (left) and CPMV-scIAA-sBio (right). Arrows point to localization of the gold particles around the CPMV. Scale bar is 50 nm.

Virus particle multimers and methods of making and using such virus particle multimer are described herein. Virus particle multimers are constructed by preparing a plurality of asymmetrically functionalized virus particles bearing one or more functional groups and contacting the asymmetrically functionalized virus particles with a first linker molecule that reacts with the functional groups to form a virus particle multimer that includes a plurality of asymmetrically functionalized virus particles connected by the linker molecule. The asymmetrically functionalized virus particles can be prepared by attaching the virus particles to a support surface to allow asymmetrical functionalization to be introduced. The virus particles retain reactive sites that can be used to attach other molecules, such as cargo molecules and targeting molecules. Examples of cargo molecules include imaging agents and therapeutic agents. Virus particle multimers exhibit significantly more uptake by cells, in comparison with single virus particles, while virus particle multimers bearing targeting molecules such as RGD show significantly increased affinity.

Definitions

It is to be understood that this invention is not limited to particular methods, reagents, compounds, compositions or biological systems, which can, of course, vary. It should also be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups. Cyclic groups can be monocyclic or polycyclic and preferably have from 3 to 10 ring carbon atoms.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

As used herein, a carboxyl moiety (COOH) includes a hydroxyl moiety attached to a carbonyl group. A sulfonic moiety ($SO_3H$) is the defining portion of a sulfonic acid, and a phosphonic moiety ($PO_3H_2$) is the defining portion of a phosphonic acid.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

A "cargo molecule," as used herein, refers to a small organic or inorganic molecule, such as a drug or imaging agent, that can be associated with a virus particle multimer in order to confer an additional function on the virus particle multimer.

A "linker molecule," as used herein, refers to a molecule including linker region made up of a long hydrophilic carbon chain or hydrophilic polymer, and two or more attachment sites provided at the ends of the linker molecule that allow the linker to be reacted with virus particles and/or attachment sites on a support surface.

"Image" or "imaging" refers to a procedure that produces a picture of an area of the body, for example, organs, bones, tissues, or blood.

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

Contacting, as used herein, refers to causing two items to become physically adjacent and in contact, or placing them in an environment where such contact will occur within a short timeframe. For example, contacting a virus particle with a cargo molecule includes placing the virus particle and the cargo molecule in solution where they will rapidly associate through random motion within the solution.

"Pharmaceutically acceptable" as used herein means that the compound or composition is suitable for administration to a subject for the methods described herein, without unduly deleterious side effects.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

As used herein, the term "effective amount" refers to an amount of an agent that is sufficient to provide a desired effect. For example, a "diagnostically effective amount" enables the imaging of the contrast agent in cells, tissues, or organisms using imaging equipment, while a "therapeutically effective amount" provides an amount that is effective to reduce or arrest a disease or disorder such as abnormal cell growth in a subject. The result can be a reduction and/or alleviation of the signs, symptoms, or causes of a disease or disorder, or any other desired alteration of a biological system. An effective amount in any individual case may be determined by one of ordinary skill in the art using routine experimentation.

In one aspect, the present invention provides a method of making a virus particle multimer. Another aspect of the invention relates to virus particle multimers prepared according to this method. The method includes preparing a plurality of asymmetrically functionalized virus particles bearing one or more functional groups, and contacting the asymmetrically functionalized virus particles with one or more first linker molecules. The linker molecules react with the functional groups on the virus particles to form a virus particle multimer that includes a plurality of asymmetrically functionalized virus particles connected by the one or more linker molecules. The term "multimer," as used herein, refers to an assembly of at least two virus particles. The multimers generally have at least two asymmetrically functionalized virus particles connected via one or more first linker molecules. In various embodiments, the multimer can include 2, 3, 4, or more connected asymmetrically functionalized virus particles. Multimers including only two asymmetrically functionalized virus particles are referred to herein as dimers. The multimers can be connected in various configurations. Preferably the multimers are connected in a linear configuration, although some multimers can be connected in a branched configuration.

Virus Particles

The viral particle multimers of the present invention can be formed using a variety of different types of virus particles. The invention makes use of virus particles as nanoparticles, which can be regarded as nature's carrier system and are also biodegradable and non-infectious in mammals. This provides a method for assembling nanoparticle multimers that can be performed at physiological pH and does not require harsh organic solvents, but also provides biomedically relevant nanoparticles. Viral particles are easily modifiable through both genetic engineering and chemical modification, with a well-ordered, multivalent display of functional groups on the exterior as well as the interior surface. Pokorski et al., Mol. Pharm., 8 (1), 29-43 (2011). They are also highly economical as production can be scaled up using molecular farming or fermentation. However, while there are many advantages to using virus particles, in some embodiments it may be preferable to use virus-like particles such as a protein nanocage rather than true virus particles.

Use of the terms "virus" and "virus particle" are used interchangeably herein. Virus particles include a number of capsid proteins that are assembled to form a protein cage, within which may be the nucleic acid encoding the virus. Note that the viruses and virus particles described herein may or may not include a nucleic acid within the protein cage.

With regard to the present invention, virus particles are categorized based on their source and structure. For example, virus particles from mammalian, avian, bacterial, or plant sources can be used. One advantage of using viruses from plant sources is that they can be readily cultivated, and are unlikely to cause infection when used in vivo in a subject. In addition, virus particles having a helical, icosahedral, or prolate structure can be used. Preferably, the virus particles used are non-enveloped virus particles. Examples of helical viruses include tobaviruses such as tobacco mosaic virus and filamentous bacteriophages, e.g. M13 and fd. A variety of helical viruses are described by Stubbs et al., Adv. Exp. Med. Bio., 726, p. 631-658 (2012), the disclosure of which is incorporated herein by reference. Examples of icosahedral viruses include Q13, P22 and other bacteriophages, HIV, herpesvirus, adenovirus, poliovirus, human papillomavirus, and picornaviruses, as well as various plant viruses such as cowpea mosaic virus, brome mosaic virus, cowpea chlorotic mottle virus, etc.

In some embodiments, the virus particle multimers are formed from plant picornaviruses. A plant picornavirus is a virus belonging to the family Secoaviridae, which together with mammalian picornaviruses belong to the order of the Picornavirales. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus comovirus. A preferred example of a comovirus is the cowpea mosaic virus.

The cowpea mosaic virus (CPMV) was selected as the model system for preparing viral particle multimers herein. CPMV is made up of 60 copies of an asymmetric unit composed of a large (L) and small (S) coat protein arranged into an icosahedral structure with pseudo T=3 symmetry. There are 5 addressable lysine side chains per asymmetric unit on its exterior surface, for a total 300 reactive groups.
Preparation of Asymmetrically Functionalized Virus Particles Viral particle multimers are prepared by linking together a plurality of asymmetrically functionalized virus particles. By functionalized, what is meant is that one or more functional groups have been attached to the virus particle. Functional groups, as used herein, are molecules providing a particular reactive moiety that can be used to bind the virus particles to particular linker molecules. Examples of functional groups include reactive alkenes, alkynes, amines, amides, alcohols, esters, ketones, halogens, acyl halides, aldehydes, thiols, phosphate groups, or carboxylic acid moieties. Asymmetric functionalization refers to the fact that the functional groups are present primarily on one side of the virus particle. The side not bearing a significant number of functional groups will still retain reactive sites natural to the virus particle, and these can serve as attachment sites for various other compounds such as cargo molecules or targeting molecules. Asymmetric functionalization helps control cluster formation of the particles and preventing undesirable aggregation. In different embodiments, the functional groups can be clustered more or less closely around a pole (a central point on one side) of the virus particle. For example, the functional groups can be found on about 10%, 25%, or 50% of the virus particle surface, with the percentage representing the portion of the extent from the pole of the virus particle over which the functional groups can be found. In some embodiments, the virus particle may only bear a single functional group.

Asymmetrically functionalized virus particles can be prepared by binding the virus particles to a support surface. Binding the virus particles to a support surface facilitates creation of asymmetric functionalization by shielding the proximal side of the virus particle, or by providing functionalization where attachment occurs. A support surface, as defined herein, is a surface bearing attachment sites which have the capacity to bind to reactive sites or functional sites on the surface of the virus particles. The surface should generally provide a high degree of hindrance from one direction so as to shield virus particles attached to the surface from reaction in from that direction. An example of a support surface is a solid-state support such as a resin.

Figure 1:
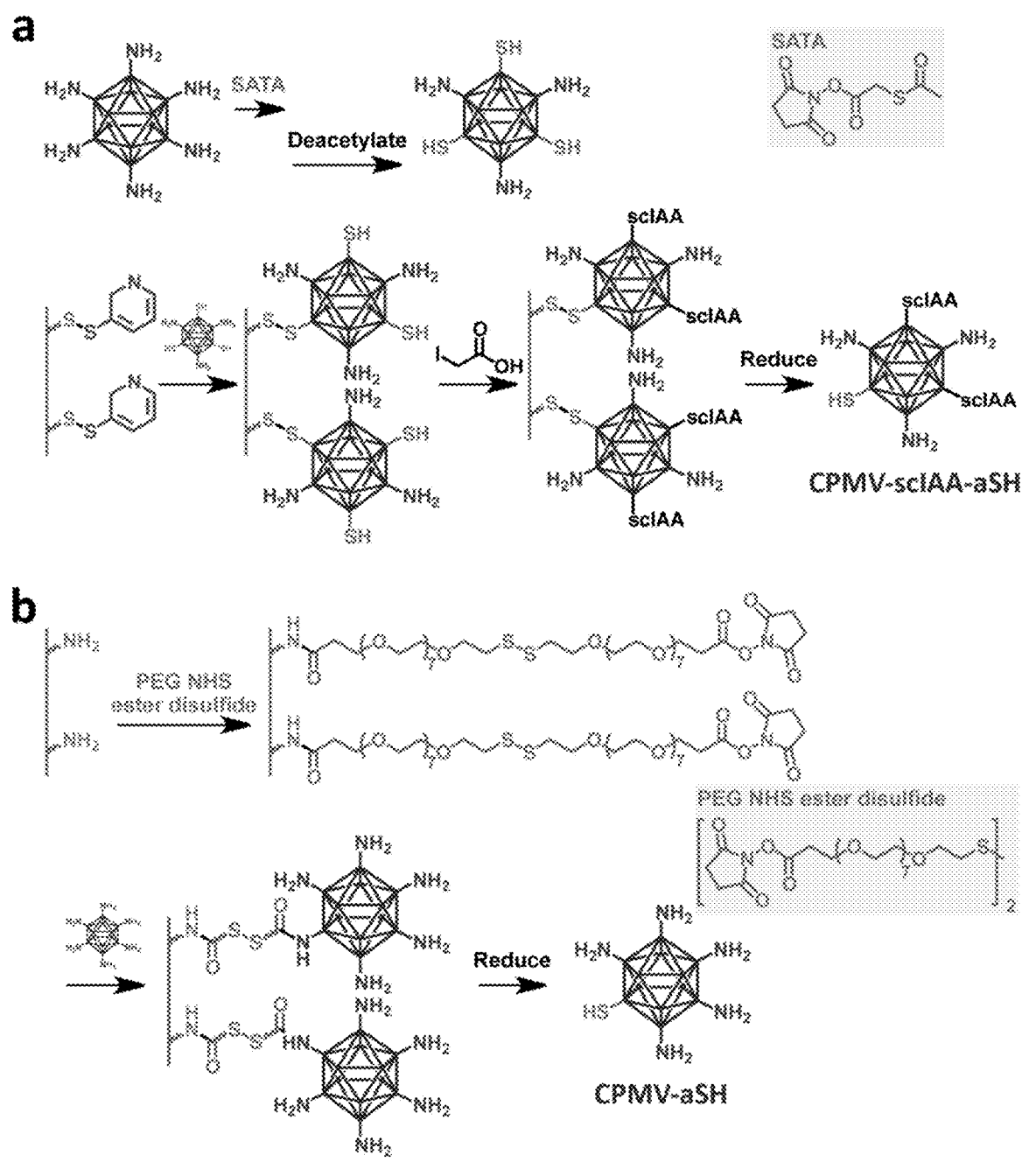

In one embodiment, as shown in FIG. 1a, the virus particle is first reacted with a functional group compound, which modifies a portion of the reactive sites on the surface of the virus particle to form functional groups. For example, the amine group of lysines present on the surface of the virus particle can be reacted with N-succinimidyl S-acethylthioacetate (SATA) to form thiol functional groups. The concentration of the functional group compound can be used to vary the portion of reactive sites which are modified to form functional groups; e.g., a higher concentration can be used to modify a higher percentage of the reactive sites. The virus particle is then bound to the support surface, preferably but not necessarily by binding of the functional group to an attachment group on the support surface. The bound virus particle is then treated with a passivating agent to block functional groups on the distal side of the bound virus particle, away from the support surface. As is understood by those skilled in the art, a passivating agent is a reactant suitable for converting reactive sites (in this case, functional groups) into an inert form to prevent their further reaction. Common inert forms are alky groups that do not present a reactive moiety. Selection of the particular passivating agent will depend on the nature of the reactive site being passivated. The bound virus particle is then released from the support surface by cleaving the bond between the functional group and the attachment group, providing an asymmetrically functionalized virus particle, bearing one or more functional groups on the side of the virus particle that was proximal to the support surface before cleavage of the virus particle from the support surface, while the functional groups on the side of the virus particle that was distal to the support surface are blocked as a result of reaction with the passivating agent.

In another embodiment, the asymmetrically functionalized virus particles are prepared by attaching a plurality of virus particles to attachment sites on the support surface through one or more reactive sites, chemically converting a portion of the remaining reactive sites on the virus particles to functional groups to form asymmetrically functionalized virus particles, and releasing the asymmetrically functionalized virus particles from the support surface. Asymmetrically functionalized virus particles can be prepared by shielding one side of the virus particle with a support surface, and then adding functional groups to an unshielded portion of the virus particle. More specifically, a plurality of virus particles are reacted with attachment groups on a support surface (e.g., a solid-state support) to create a plurality of bound virus particles, chemically converting a portion of the remaining reactive sites on the virus particles to functional groups to form asymmetrically functionalized virus particles, and then releasing the asymmetrically functionalized virus particles from the support surface.

Alternately, in some embodiments the functional groups of the asymmetrically functionalized virus particle are attached to the virus particle through a linker molecule, in particular a second linker. An embodiment making use of a second linker molecule is shown in FIG. 1b. This results in the functional molecule being extended from the surface of the virus particle by all or a portion of the second linker. A plurality of second linker molecules including a functional group are attached to a support surface using the attachment sites on the linkers and support surface, and then reacting a plurality of virus particles with the attached second linker molecules. The types of chemistry used to carry out the attachment are the same as those described herein for the first linker molecules. Upon attachment to the support surface, the second linker can be referred to as a linked functional group compound. The linked functional group retains one or more attachment sites suitable for attachment to reactive groups on the virus particles. In some embodiments, the functional group can be in the form of a functional group precursor which is later converted to a functional group by cleavage, such as a disulfide "precursor" that is converted to a sulfhydryl functional group. The second linker molecule can be functionally distinguished from the first linker molecule, which is used to connect asymmetrically functionalized virus particles to one another, as it is not used to directly connect one virus particle to another, although it can form part of such a linkage.

In principle, any long hydrophilic carbon chain, such as a hydrophilic polymer chain, that can be contacted with an aqueous solution is suitable as a linker molecule. Hydrophilic carbon chains and polymers include polar or charged functional groups that render them soluble in water. Examples of such hydrophobic polymers include acrylic acid, acrylamide, maleic anhydride polymers, polyethylene glycol, and copolymers. Polyethylene glycol is a particularly suitable linker molecule. The second linker preferably has a length no greater than the diameter of the virus particles being used. The second linker molecules are then cleaved to provide a plurality of asymmetrically functionalized virus particles, which in this embodiment of the invention retains a portion of the second linker molecule between the virus particle and the functional group.

Carrying out the reaction in the manner shown in Figure 1b provides a couple advantages. First, by providing a point of attachment for the virus particle that is some distance from the support surface, the ease with which virus particles are attached is increased. Second, by retaining a linker region on the asymmetrical virus particle between the virus particle and the functional group, the ease with which asymmetrical virus particles can subsequently be bound to one another is also improved. Note that the linker is not actually shown in Figure 1b; nonetheless, it would be present between the —SH group and the virus particle itself. While only a single functional group is shown in FIG. 1b, it is possible for a single virus particle to become attached through multiple reactive sites to multiple linked functional group compounds, thereby resulting in a virus particle including multiple functional groups when the virus particle is cleaved from the support surface. All of these functional groups will be found on the proximal side of the virus particle, relative to its binding to the support surface, thereby providing an asymmetrically functionalized virus particle which further includes a linker providing space between the functional group and the virus particle.

Preparation of Virus Particle Multimers

Viral particle multimers are prepared by linking together a plurality of asymmetrically functionalized virus particles. Because the virus particles are asymmetrically functionalized, uncontrolled crosslinking of the virus particles is avoided, and instead relatively small groups of attached virus particles, referred to herein as multimers, are formed. In some embodiments, the first linker molecule is a bifunctional linker. A bifunctional linker includes a single carbon or polymer chain, with an attachment site at each end. When a bifunctional linker is used, the asymmetrically functionalized virus particles will mainly form dimers, as a result of attachment of a virus particle at each end of the bifunctional linker, where the attachment sites are located. However, to increase the number of virus particles included in a virus particle multimer, multifunctional linker molecules can be used. Multifunctional linker molecules are linker molecules including 3 or more attachment sites for the virus particles. For example, the multifunctional linkers can include 3, 4, 5, 6, 7, 8, 9, 10, 11, 12, or more than 12 attachment points. Multifunctional linker molecules generally include a branched carbon chains or polymer as the linker region.

First linker molecules comprise a linker region and 2 or more attachment sites. The linker region is a long organic chain. Preferably, the length of the linker region of the first linker is not greater than about twice the diameter of the virus particles being used. For example, when using Cowpea Mosaic Virus particles, the linker region can have a length of 60 nm or less. The linker can be functionalized or unfunctionalized, substituted or unsubstituted, and/or linear or branched. In some embodiments, the linker molecule is a long alkyl chain, which may or may not include heteroatoms (i.e., oxygen, sulfur, and or nitrogen). A preferred linker region is polyethylene glycol, which is a long alkyl chain including oxygen heteroatoms. As described above, any long hydrophilic carbon chain, such as a hydrophilic polymer chain, that can be contacted with an aqueous solution is suitable as a linker molecule. Attachment sites should be chosen that have complementary chemistry with the functional sites provided on the asymmetrical virus particles. For example, maleimide attachment sites may be provided at the ends of linker regions in order to provide first linker molecules that will bond to asymmetrical virus particles including thiol functional groups. Other pairs include, but are not limited to, N-hydroxysuccinimde-amine, alkyne-azide, amine-carboxylate, where either functional group could be presented on the asymmetric nanoparticle or as terminal part of the linker. Further, combinations of heterofunctional linkers can be used; e.g. one could use a four arm linker in which two arms display an amine-functional group and two other arms would present alkyne functional groups.

Cargo Molecules

A virus particle multimer can be loaded with one or more cargo molecules. In some embodiments, the cargo molecule is loaded by covalently attaching the cargo molecule to a reactive molecule on a surface (interior or exterior) of one or more virus particles of the virus particle multimer. In other embodiments, the virus particle multimer is loaded with cargo molecules that associate with nucleic acid carried within the virus particle. Preferably, the virus particle multimer is loaded with a plurality, or a substantial number of cargo molecules. For example, in some embodiments, from about 50 to about 500 cargo molecules are loaded per virus particle multimer, while in other embodiments from about 50 to about 200 cargo molecules are loaded per virus particle multimer.

A variety of different types of cargo molecules can be loaded into the virus particles. Cargo molecules are generally relatively small organic or inorganic molecules. In some embodiments, the cargo molecules have a molecular weight ranging from about 50 to about 5000 daltons, with some embodiments being directed to cargo molecules having a weight ranging from about 50 to about 1000 daltons, or from about 100 to about 500 daltons. Examples of cargo molecules are imaging agents and therapeutic agents such as antitumor agents.

Imaging and Therapeutic Agents

In some embodiments, the virus particle multimer is modified to carry an imaging agent. Examples of imaging agents include fluorescent compounds, radioactive isotopes, and MRI contrast agents. For example, in some embodiments, the imaging agent is a fluorescent molecule for fluorescent imaging. The imaging agent can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Means of detecting imaging agents are well known to those of skill in the art. Thus, for example, where the imaging agent is a radioactive compound, means for detection include a scintillation counter or photographic film as in autoradiography. Where the imaging agent includes a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

Examples of imaging agents that can be used as cargo molecules for virus particle multimers include magnetic beads (e.g. Dynabeads™), fluorescent dyes (e.g., fluorescein isothiocyanate, AlexaFluor555, Texas red, rhodamine, and the like), radiolabels (e.g., $^{3}$H, $^{14}$C, $^{35}$S, $^{125}$I, $^{121}$I, $^{112}$In, $^{99m}$Tc), other imaging agents such as microbubbles (for ultrasound imaging), $^{18}$F, $^{11}$C, $^{15}$O, (for Positron emission tomography), $^{99m}$TC, $^{111}$In (for single photon emission tomography), and chelated lanthanides such as terbium, gadolinium (e.g., chelated gadolinium), and europium or iron (for magnetic resonance imaging). The choice of imaging agent depending on sensitivity required, ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III). Gadolinium contrast agents are generally chelated to facilitate attachment to the virus particle. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA).

In other embodiments, the cargo molecule is a therapeutic agent. Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., anti-ulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppres sant drugs, and antitumor agents.

In some embodiments, the therapeutic agents used as cargo molecules are small molecule antitumor agents. One advantage of using antitumor agents as cargo molecules is the ability of virus particles to preferentially associate with tumor cells. Examples of small molecule antitumor agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-a, rapamycin, thapsigargin, and bikunin, and derivatives thereof.

Attachment of Cargo Molecules

Cargo molecules can be conjugated to virus particle multimers by any suitable technique, with appropriate consideration of the need for pharmacokinetic stability and reduced overall toxicity to the patient. The term "conjugating" when made in reference to an agent and a virus particle multimer as used herein means covalently linking the agent to the virus subject to the limitation that the nature and size of the agent and the site at which it is covalently linked to the virus particle do not interfere with the biodistribution of the modified virus. The cargo molecule can be linked to the interior or the exterior of virus particles of the multimer, while in some embodiments the cargo molecule is linked to both the interior and the exterior of the virus. The location of the cargo molecule on the interior or exterior is governed by the amino acids of the viral coat protein that are selected as reactive sites. Because asymmetrically functionalized virus particles are used to prepare the virus particle multimers, a number of reactive sites which were not converted to functional groups will remain on the surface of the virus particles, which provide convenient attachment points for cargo molecules.

Cargo molecules can be coupled to a virus particle multimer either directly or indirectly (e.g. via a binder group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g. alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

Alternatively, a suitable chemical binder group can be used. A binder group can serve to increase the chemical reactivity of a substituent on either the agent or the virus particle, and thus increase the coupling efficiency. Suitable binder chemistries include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, the surface of the virus particle multimer can be modified by attachment of something other than a cargo molecule. For example, the virus particle multimer can be modified to include PEGylation, cell penetrating peptides, or targeting molecules. The virus particle multimer can be modified either before loading with cargo molecules, or after loading with cargo molecules. Targeting molecules can be attached to the outside of the virus particle multimer in order to guide the multimers to a particular target tissue, such as tumor tissues. Examples of targeting molecules include peptide ligands (e.g., RGD, bombesin, or GE11), vitamins such as folic acid, and other tumor-homing proteins such as transferrin, as well as and antibodies such as Herceptin or any other antibody or antibody fragment with tumor-specific properties, and DNA-, RNA-, or PNA-based aptamers that specifically bind to an antigen present on the target tissue, such as a tumor antigen. Cell penetrating peptides can also be attached to the outside of the virus particle multimers to encourage internalization of the multimers. Cell penetrating peptides are generally relatively short, amphipathic peptides. Examples of cell penetrating peptides include TAT sequence or polyArginine peptides.

In some embodiments, rather than covalent attachment, cargo molecules can also be loaded into virus particle multimers in a non-covalent manner by associating them with nucleic acid present within the viral particle capsid. While not intending to be bound by theory, it appears that the cargo molecule associates with the nucleic acid as a result of the affinity of the cargo molecule for the nucleic acid. Affinity is the tendency of a compound to naturally associate with another object (e.g., a nucleic acid). Affinity is influenced by non-covalent intermolecular interactions between the compound and the object, such as hydrogen bonding, electrostatic interactions, hydrophobic interactions, and Van der Waals forces. As used herein, a compound is considered to have affinity for nucleic acid within the virus particle if it exhibits a dissociation constant of at least one micromolar with regard to the viral nucleic acid.

An example of cargo molecules having an affinity for the nucleic acid are cargo molecules having a positive charge. One skilled in the art can readily determine whether a cargo molecule has affinity for the nucleic acid within a plant virus particle. For example gel mobility shift assays, oligonucleotide crosslinking assays, optical absorbance and fluorescence assays, calorimetric assays, and/or surface Plasmon resonance assays to determine the association and dissociation kinetics and affinities of cargo molecules for nucleic acids. Furthermore, any drug or imaging agent exhibiting low affinity can be readily modified with a small, positively charged tag or complementary oligonucleotide to bind to nucleic acid within a virus particle. For some embodiments, it is also preferable that the cargo molecules interact with nucleic acids in a reversible manner, in order to facilitate release of the cargo molecules in the target tissue subsequent to internalization.

Targeting Molecule

In some embodiments, a targeting molecule can also be attached to virus particle multimers. By "targeting molecule" herein is meant a molecule which serves to target or direct the virus particle to a particular location, cell type, diseased tissue, or association. In general, the targeting molecule is directed against a antigenic site. Thus, for example, antibodies, cell surface receptor ligands and hormones, lipids, sugars and dextrans, alcohols, bile acids, fatty acids, amino acids, peptides and nucleic acids may all be attached to localize or target the virus particle multimer to a particular site. In some embodiments, the targeting molecule allows targeting of the virus particle multimers to a particular tissue or the surface of a cell. Preferably, the targeting molecule is linked to a reactive site on the exterior surface of the virus to provide easier access to the antigenic site. Virus particle multimers including targeting molecules exhibit increased affinity for target cells including the chosen antigenic site, as compared with single virus particles including target molecules.

In some embodiments, the targeting molecule is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting molecule is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', Fab')$_2$ or other antigen-binding subsequences of antibodies) which contain minimal sequence derived from non-human immunoglobulin.

In some embodiments, the antibody is directed against a cell-surface marker on a cancer cell; that is, the antigenic site is a cell surface molecule. As is known in the art, there are a wide variety of antibodies and antibody fragments known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting molecule is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

In some embodiments, the virus particle multimer can be directed to a target tissue in a subject without the use of a targeting molecule, based on the ability of virus particles to preferentially accumulate in certain tissues. In particular, virus particles have been shown to preferentially accumulate in diseased tissue, such as cancer tissue or inflamed tissue (e.g., atherosclerotic blood vessels). While not intending to be bound by theory, it appears that virus particles are taken up by blood components such as macrophage cells of the immune system, which subsequently accumulate in diseased tissue (e.g., a tumor or atherosclerotic blood vessel), thereby delivering the virus particle to cells at the disease site.

Pharmacokinetics and Immune Response to Virus Particles

In some embodiments, administering the virus particle multimer to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the virus particle multimer is typically undesirable. Accordingly, in some embodiments it may be preferable to modify the multimer or take other steps to decrease the immune response. For example, an immunosuppressant compound can be administered to decrease the immune response. More preferably, the virus particle multimer can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the virus particle multimer is decreased by PEGylation to provide a PEGylated virus particle. PEGylation is the process of covalent attachment of polyethylene glycol (PEG) polymer chains to a molecule such as a virus particle multimer. PEGylation can be achieved by incubation of a reactive derivative of PEG with the multimer. The covalent attachment of PEG to the virus particle multimer can "mask" the agent from the host's immune system, and reduce production of antibodies against the virus. PEGylation also may provide other benefits. PEGylation can be used to vary the circulation time of the virus particle multimer.

The first step of PEGylation is providing suitable functionalization of the PEG polymer at one or both terminal positions of the polymer. The chemically active or activated derivatives of the PEG polymer are prepared to attach the PEG to the virus particle multimer. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Imaging and Therapeutic Use of Loaded Virus particles

In one aspect, the present invention provides a method of delivering a cargo molecule to a cell, comprising contacting the cell with a virus particle multimer loaded with the cargo molecule. Various different embodiments of the method of delivering a cargo molecule using virus particles multimers loaded with the cargo molecule are envisioned. In some embodiments, the cargo molecule is a therapeutic agent such as an antitumor agent, while in other embodiments, the cargo molecule is an imaging agent. One of the advantages of virus particle multimers, which is relevant for either use, is that they are taken up by cells more readily than single virus particles. While not intending to be bound by theory, this may be due to the lower entry barrier for a multimer, resulting from increased attachment points on the cell and/or a lower surface tension barrier. Other advantages of virus multimers (as non-spherical materials) are enhanced pharmacokinetic and flow properties, as well as reduced clearance by macrophages.

In one embodiment, the method includes generating an image of a tissue region of a subject, by administering to the subject a diagnostically effective amount of a virus particle multimer having an imaging agent linked to the virus particle multimer, and generating an image of the tissue region of the subject to which the virus particle multimer has been distributed. In order to generate an image of the tissue region, it is necessary for an effective amount of imaging agent to reach the tissue region of interest, but it is not necessary that the imaging agent be localized in this region alone. However, in some embodiments, the virus particle multimers bearing imaging agents are targeted or administered locally such that they are present primarily in the tissue region of interest. When used to detect or image cancer cells in a cell culture, one skilled in the art should be able to vary the exposure time, the amount of loaded virus particle and the final concentration to optimize the detection or imaging desired. Other experimental parameters may be varied to achieve the other effect, depending on the specific experiment conducted, and identification of such parameters should involve minimal experimentation by those skilled in the art.

Examples of images that can be produced through the use of virus particle multimers including an imaging agent include two-dimensional cross-sectional views and three dimensional images. In some embodiments, a computer is used to analyze the data generated by the imaging agents in order to generate a visual image. The tissue region can be an organ of a subject such as the heart, lungs, or blood vessels. In other embodiments, the tissue region can be diseased tissue, or tissue that is suspected of being diseased, such as a tumor or atherosclerotic tissue. Examples of imaging methods include computed tomography, positive emission tomography, and magnetic resonance imaging, and optical or fluorescence imaging.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

The compositions of the invention can be used for the imaging and detection of target cells in cell cultures and in vivo. The compositions of the invention can also be used for the imaging and detection of target cells in organs and tissues ex vivo. Examples of target cells include cancer cells, cells involved in inflammation, and vimentin-expressing cells. The compositions of the invention can also for killing or growth prevention of cancer cells, provided that the compositions include a therapeutic agent that is capable of killing or stopping the growth of cancer cells once internalized by them.

Another aspect of the invention provides a method of delivering a therapeutic agent to a target cell. Examples of target cells include tumor cells and cells involved in inflammation. However, virus particles can be modified for targeting to a variety of different issues by modifying the virus particle multimer to include a targeting molecule such as antibodies that specifically bind to an antigen present on the target tissue. The method includes contacting the cell with a virus particle multimer loaded with cargo molecules, prepared as described, wherein the cargo molecules are released within the cell subsequent to internalization of the virus particle multimer by the cell.

In some embodiments, the cell contacted with the virus particle multimer is a cancer cell. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the loaded virus particles including antitumor compounds are used to treat or image cancer tissue selected from the group consisting of colon cancer, brain cancer, breast cancer, fibrosarcoma, and squamous carcinoma. A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

In other embodiments, the virus particle multimers can be used to target inflamed tissue, such as atherosclerotic tissue. Atherosclerosis is a chronic inflammatory response in the walls of arteries, caused largely by the accumulation of macrophages and white blood cells and promoted by low-density lipoproteins (LDL, plasma proteins that carry cholesterol and triglycerides) without adequate removal of fats and cholesterol from the macrophages by functional high-density lipoproteins (HDL). It is commonly referred to as a hardening or furring of the arteries, and is caused by the formation of multiple plaques within the arteries, which can be detected by MRA.

In many embodiments, the virus particle multimer is used to treat or image cells that are in vivo. However, it should be appreciated that all the preceding and following therapeutic applications may also be performed in an "ex vivo" manner. In this case, a tissue or organ in which detection or killing of cancer cells is desired may be removed from an organism, under conditions which allows the tissue or organ to remain viable and with minimal alteration of the natural conditions of the tissue or organism. The procedure should usually be conducted under sterile conditions to minimize possibility of contamination. The tissue or organ may be exposed to the composition of the invention for a variable amount of time, from minutes to days. The compositions of the invention may be provided as suspensions, powders, pastes or other suitable presentations, and the mode of contact between the composition of the invention and the tissue or organ should be such that detection or killing of cancer cells is achieved. Those skilled in the art should be able to determine the optimal contact time without undue experimentation. Once the desired detection or killing of cancer cells is achieved, the tissue or organ may be returned to the original organism or to another organism in need to such tissue or organ. Transplantations should proceed following the procedures known by those skilled in the art.

Dosage and Formulation of Loaded Virus particles

When used in vivo, the virus particle multimers are preferably administered as a pharmaceutical composition, comprising a mixture, and a pharmaceutically acceptable carrier. The virus particle multimers may be present in a pharmaceutical composition in an amount from 0.001 to 99.9 wt %, more preferably from about 0.01 to 99 wt %, and even more preferably from 0.1 to 95 wt %.

The virus particle multimers, or pharmaceutical compositions comprising these multimers, may be administered by any method designed to provide the desired effect. Administration may vary depending on whether or not the multimers are being used for imaging or for a therapeutic effect. Administration may occur enterally or parenterally; for example orally, rectally, intracisternally, intravaginally, intraperitoneally or locally. Parenteral and local administrations are preferred. Particularly preferred parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device. Suitable forms of local administration include powders, ointments, suspensions and drops.

The compositions can also include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The pharmaceutical compositions of this invention can include parenteral administration, such as administration into a body cavity or lumen of an organ. The compositions for administration will commonly comprise a suspension of the virus particle multimers in a pharmaceutically acceptable carrier, preferably an aqueous carrier. A variety of aqueous carriers can be used, e.g., buffered saline and the like. These suspensions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The amount of the virus particle multimer in these formulations can vary widely, and will be selected primarily based on fluid volumes, viscosities, body weight and the like in accordance with the particular mode of administration selected and the subject's needs.

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

A typical pharmaceutical composition for intravenous administration would be about 0.1 to 10 mg per kg of body weight per subject per day. However, dosages from 0.1 up to about 100 mg per kg of body weight per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., 1980, Mack Publishing Company, Easton, Pa.

The formulations may be conveniently presented in unit dosage form and may be prepared by any of the methods well known in the art of pharmacy. Preferably, such methods include the step of bringing the virus particle multimers into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, in an amount effective to produce the desired effect. Single or multiple administrations of the compositions may be administered depending on the dosage and frequency as required and tolerated by the subject. In any event, the administration regime should provide a sufficient quantity of the composition of this invention to effectively treat the subject.

For multimers loaded with an antitumor agent, an exemplary treatment regime entails administration once per every two weeks or once a month or once every 3 to 6 months. The composition including the virus particle multimers is usually administered on multiple occasions. Alternatively, the virus particle multimers can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of cancer.

One skilled in the art can readily determine an effective amount of virus particle multimer composition to be administered to a given subject, by taking into account factors such as the size and weight of the subject; the extent of disease penetration; the age, health and sex of the subject; the route of administration; and whether the administration is local or systemic. In the case where the construct comprises a therapeutic agent meant to selectively kill cancer cells, the amount of virus particle to be administered to a subject depends upon the mass of cancer cells, the location and accessibility of the cancer cells, and the degree of killing of cancer cells caused by the therapeutic agent. Useful dosages of the virus particle multimers can be determined by comparing their in vitro activity and the in vivo activity in animal models. Methods for extrapolation of effective dosages in mice, and other animals, to humans are known in the art. Those skilled in the art may derive appropriate dosages and schedules of administration to suit the specific circumstances and needs of the subject. For example, suitable doses of virus particles to be administered can be estimated from the volume of cancer cells to be killed.

The present invention is illustrated by the following examples. It is to be understood that the particular examples, materials, amounts, and procedures are to be interpreted broadly in accordance with the scope and spirit of the invention as set forth herein.

EXAMPLES

Example 1: Assemblies of Viral Nanoparticles and their Enhanced Cell Uptake Properties A novel polymer-mediated method for the fabrication of small nanoparticle assemblies is presented. This approach is demonstrated for the construction of a range of clusters and chains of nanoparticles. The ability for controlled formation of networks of various architectures on the nanoscale using this modular bottom-up approach will allow for new nanomedical and nanoelectronic applications in drug delivery, imaging, and sensing. As an initial demonstration of the possibilities afforded by nanoparticle assemblies, cell uptake was evaluated and was found to be elevated for dimers compared to single particles, particularly for particles displaying RGD targeting molecules specific for integrins expressed on cancer cells.

Symmetry Breaking. In order to tightly control cluster formation of the particles without undesirable aggregation, it is necessary to first form asymmetric particles where functional groups for conjugation are only available on one side of the particle. In other words, these symmetry-broken nanoparticles have janus-type character. Two methods were applied to synthesize symmetry-broken CPMV, which are illustrated in FIG. 1. Briefly, in the first method, thiols with a protective acetate group were introduced all around the exterior lysines of CPMV via N-hydroxysuccinimide (NHS) ester chemistry (CPMV-SATA). This prevents disulfide bond formation and interparticle linkage between individual CPMV nanoparticles during storage. Steinmetz et al., ChemBioChem, 8 (10), 1131-1136 (2007). After deacetylation (CPMV-SH), the particles were bound to a thiol-activated solid-phase support through disulfide bond formation, with subsequent passivation of the remaining, unbound thiols using iodoacetic acid (IAA). Klem et al., J. Am. Chem. Soc., 125 (36), 10806-10807 (2003) Symmetry-broken particles were obtained after release from the support under reducing conditions to yield CPMV-scIAA-aSH.

For the second method, an excess of polyethylene glycol (PEG) NHS ester homobifunctional linkers containing disulfide bonds was used to react with an amine-functionalized solid support. CPMV was then bound to the support through its exterior lysine groups. Reduction of the disulfide bonds in the linkers using TCEP resulted in asymmetric particles with thiol groups introduced on one side of the particles (CPMV-aSH). Due to the topography of CPMV, with its lysines presented close to the surface of the particle, efficiency of conjugation to the solid support is dependent on the linker size. Negligible binding of CPMV was found when 3,3'-dithiobis(sulfosuccinimidylpropionate) (DTSSP), a shorter 1.2 nm linker without the PEG spacer, was used instead of our chosen alternative linker with a 7 PEG spacer on either side.

For the first method, titration was first carried out to control for the quantity of protected thiols introduced around CPMV. Following purification of the particles and deacetylation, a maleimide-functionalized Alexa Fluor 647 fluorophore and UV/visible spectroscopy were used to estimate the number of thiol groups attached to CPMV. A 1000 molar excess of SATA to CPMV was used for an initial 25-30 thiol groups inserted onto the particle. After binding to the solid phase and passivation of the free groups, approximately 10 thiol groups remained on one face of CPMV. To verify complete passivation with the IAA, the thiols of CPMV-SH and CPMV-scIAA-aSH were functionalized with biotin to form CPMV-sBio and CPMV-scIAA-sBio, respectively, followed by the addition of avidin or immunogold staining (FIG. 2). By visual inspection as well as TEM imaging, it was clear that the symmetrical CPMV-sBio particles formed large aggregates with the introduction of avidin resulting from continuous avidin-biotin interactions, while the symmetry-broken CPMV-scIAA-sBio particles remained well dispersed. In addition, immunogold staining using 5 nm gold-labeled anti-biotin revealed binding on only one side of the asymmetric CPMV particles, compared to all around for the symmetrical CPMV control. For easier visualization of the gold labels, a single particle is shown in FIG. 2d. The degree of labeling was quantified over multiple images, with an average of 5 gold particles surrounding the symmetric particles and 0.5 gold particles surrounding the asymmetric particles. The orientation of the particles upon adsorption to the TEM grid dictates whether or not the biotin of the CPMV-scIAA-sBio is exposed and available for immunogold labeling, which accounts for why the average for the asymmetric particles is less than 1.

Despite the design advantage of being able to use titration to control the density of thiols attached to CPMV and consequently the availability of thiols for linking together the particles after symmetry breaking (Method 1), it was ultimately decided to proceed with Method 2 as there are more lysines available for future functionalization and applications. Furthermore, the introduced PEG spacer enhanced the coupling efficiency when joining the nanoparticles together into mesoscale assemblies (as discussed below). Nonetheless, it was successfully demonstrated that this was a viable approach for producing symmetry-broken particles.

As with the previous method, a maleimide-functionalized fluorophore coupled with UV/visible spectroscopy was used to characterize CPMV-aSH. Although native CPMV does not display any thiols on its exterior surface, some slight labeling was observed. This can be attributed to the presence of reactive cysteines in the interior of the CPMV particle. Wen et al., Biomacromolecules, 13 (12), 3990-4001 (2012). Multiple measurements were taken and the difference between the number of thiols per CPMV-aSH and CPMV, respectively, was considered. It was determined that an average of 5 thiol groups per CPMV were introduced after binding and release from the resin. The thiols appear to be located around a single five-fold axis of CPMV near the interface of the small and large coat proteins where the most reactive lysines (Lys38 and Lys99) are located.

It is possible that the asymmetric particles themselves are able to associate over time through formation of disulfide bonds between thiols of pairs of particles. However, no significant association of the particles was observed with TEM even after several months of storage. This could be due to the position of the thiols in the cavity formed where the small and large coat proteins assemble together. The groups would thus be less exposed and not as likely to react directly with thiols on other particles.

Figure 3:
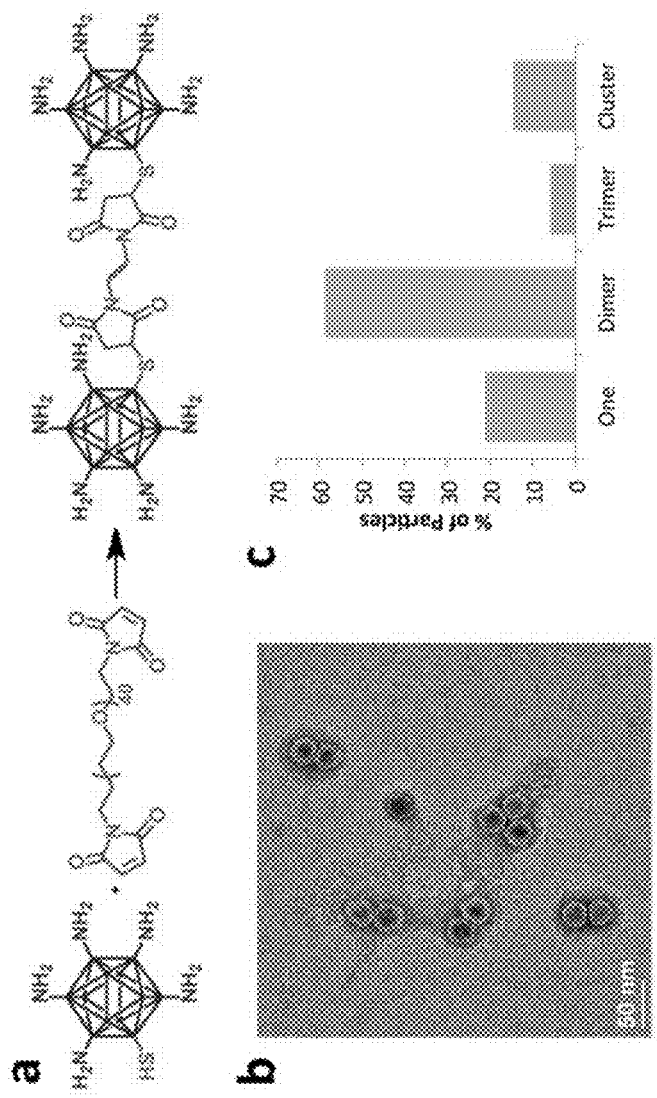
FIG. 3 provides graphs and images showing the formation of dimers using a bifunctional PEG linker. a) Reaction scheme of dimer formation. b) TEM image illustrating distribution of dimer formation. c) Statistics showing percentage of particles found as dimers compared to other arrangements, with at least 250 particles considered.

Formation of Assemblies. To determine the availability of the thiols for further conjugation, we first examined the ability to form dimers using homobifunctional maleimide PEG linkers with a molecular weight of 2000 Da (FIG. 3). Various excesses of linkers were tested and results observed using TEM. Evident dimer formation was detected when 10 molar excess of linker to CPMV-aSH was added. The reaction and TEM imaging were replicated several times, with statistics performed on the resultant arrangement of the particles and counting at least 250 particles. There was very little variation in the pattern observed, with roughly 60% of the particles found in dimers (FIG. 3c).

A few trimers and some clusters of four or more particles were also observed, which are most likely the result of the adsorption of particles near each other on the TEM grid. When considering the composition of these clusters of particles, it is of note that there is a higher statistical probability of the clusters containing dimers. For example, it is more probable for a trimer to be a combination of a dimer and a single particle rather than three individual particles, and for a tetramer to be a combination of two dimers rather than four individual particles. Regardless, to prevent bias in counting and given the lack of information, these particles were counted separately from the dimers. Based on this, it appears that the percentage of dimer formation may be underestimated. The small number of thiols introduced makes it highly unlikely that the clusters are covalently linked. Although it is possible to crosslink more than two particles with the bifunctional linkers, the small reactive surface area and steric hindrance makes it difficult to achieve.

Figure 4:
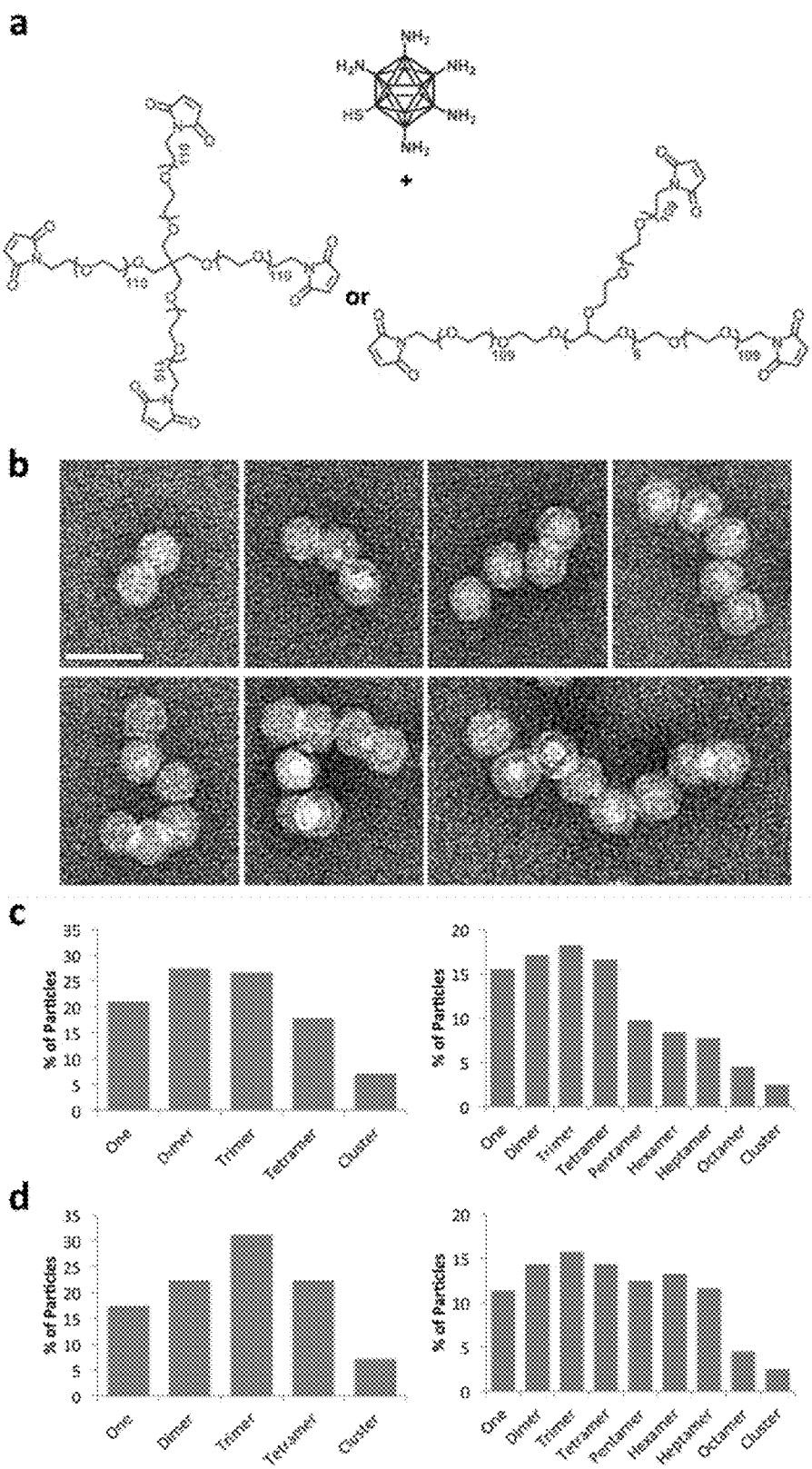
FIG. 4 provides graphs and images showing the formation of networks and chains using four-arm and eight-arm PEG linkers. a) Structure of PEG linkers used. b) TEM images showing particle arrangements of chains from one particle up to eight particles using eight-arm linker. Scale bar is 50 nm. c) Statistics showing percentage of particles found right next to each other in various configurations, with at least 250 particles considered. Reactions with four-arm PEG are shown on the left and eight-arm PEG on the right. d) Statistics of same collection of images, with relaxed requirements allowing particles to be within 30 nm of each other.

To form larger groups of particles, the inventors looked towards linkers with greater quantities of reactive groups: four-arm and eight-arm PEG maleimide with molecular weights of 20 kDa and 40 kDa, respectively (FIG. 4a). Each arm was 5000 Da (approximately 50 nm long with a Flory dimension $R_F$=6 nm) so that there was enough spacing between the arms for multiple CPMV to link together side-by-side. This was particularly important for the eight-arm PEG, where there is only 5.6 Å along the backbone between each arm. An exact stoichiometric ratio of four symmetry-broken CPMV per four-arm linker and eight per eight-arm linker was used in the coupling reactions. While lower excesses of linker resulted in many unreacted free particles, higher excesses resulted in less efficient chain and network formation as the particles are resultantly located on separate linkers. The reactions were repeated multiple times and monitored by TEM. Individual configurations are shown in FIG. 4b. Among the various batches, the results remained consistent. Histograms of the pattern of particle arrangement were formed, with a minimum of 250 particles considered for each. Given that the length of each arm of the linkers can extend up to 50 nm when fully stretched, in theory particles 100 nm apart could still be at adjacent positions attached to the same linker. Since PEG has a persistence length of 3.8 Å, approximately the length of one monomer, it behaves as a fully flexible polymer. Kienberger et al., Single Mol., 1, 123-128 (2000). Based on the flexible structure of the polymer backbone, particularly for smaller groups of particles where not every branch of the linker is occupied, it is highly possible that particles not lying right next to each other are still covalently bonded. To account for this, two approaches were considered for counting the arrangement of the CPMV (FIG. 4c-d). In one approach, the particles were required to be adjacent and touching to be considered in the same cluster, whereas in the second method the criteria was relaxed to include particles within 30 nm (one particle diameter) of each other. Representative histograms of the results from both are shown, with the exact pattern expected to be intermediate between these two distributions.

The histograms appear to resemble a Poisson distribution, with the greatest proportion of the particles coordinated into dimers or trimers for the four-arm PEG and mainly trimers for the eight-arm PEG. The distribution is broad and there is a good representation of each arrangement of particles, with at least 15% of each type of cluster for the four-arm PEG and at least 5% of each for the eight-arm PEG using the first method of counting. Using the second method, the proportion of each jumps to at least 20% and 11% (except for octamers), respectively. Although there is some ambiguity to the exact distribution of the particles, there is a clear difference in the pattern of CPMV nanoparticle cluster and chain formation based on the TEM images and respective histograms with the three different linkers.

Figure 5:
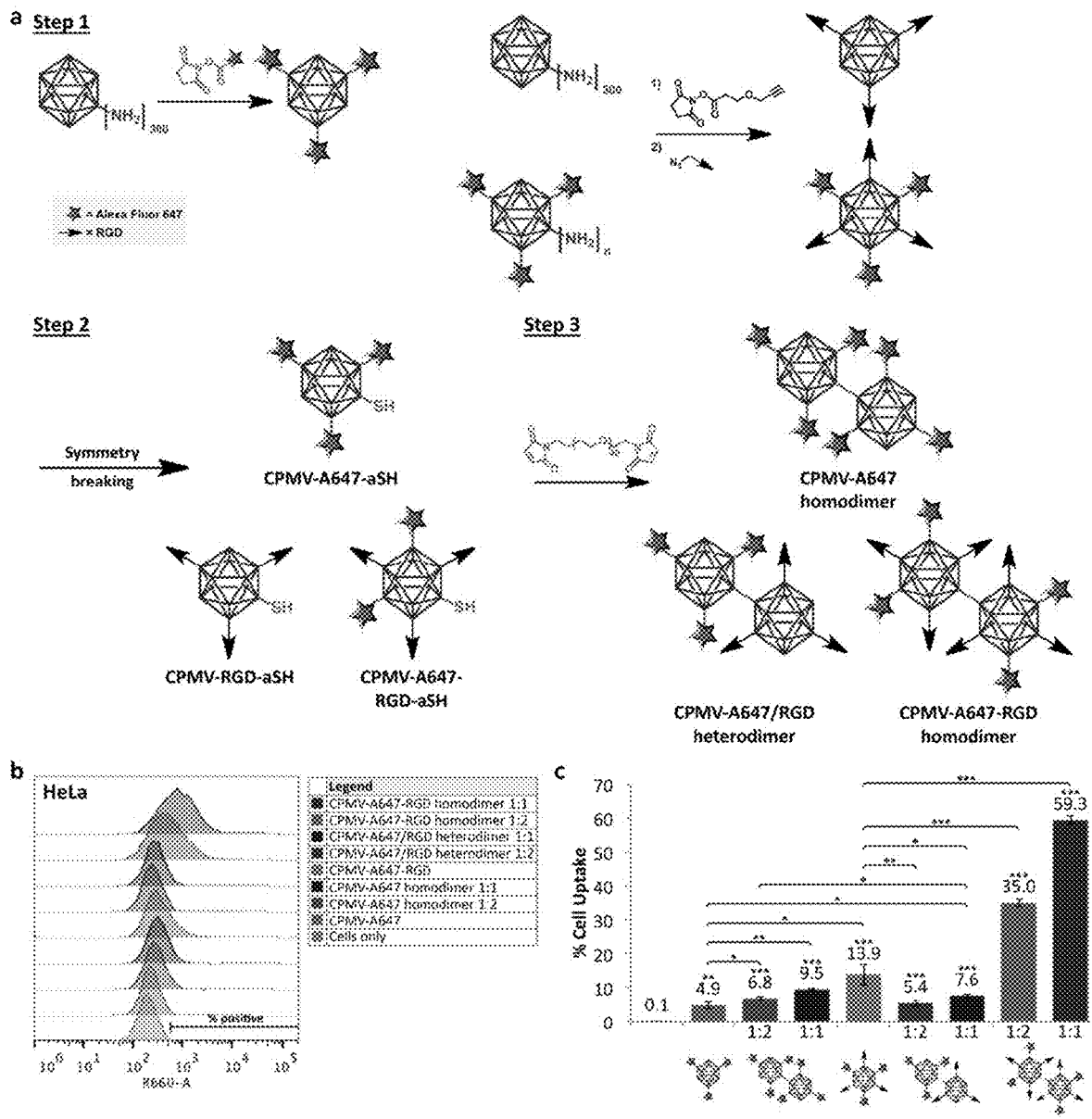
FIG. 5 provides graphs and images showing the formation of multifunctional dimers and evaluation of cellular uptake. a) Reaction schemes for dimer formation through functionalization, symmetry breaking, and dimerization. b) Flow cytometry histograms showing cell uptake. Cells to the right of the cells only control in region indicated were considered positive for particle uptake. c) Quantification of percent of positive cells (* $p<0.05$, $p<0.01$, *$p<0.001$). Unpaired asterisks denote statistical significance as compared to cells only control.

Cell Uptake Properties. To highlight the significant potential offered by the formation of nanoparticle assemblies for cell targeting applications, a systematic study of the cell uptake properties of dimers compared to single particles, both native and receptor-targeted, was performed. Single CPMV and CPMV dimers were modified to display the fluorescent dye Alexa Fluor 647 (A647) for tracking and either did or did not include a cyclic RGD integrin ligand for cell targeting. RGD is a well-known peptide motif that effectively targets integrin $\alpha_v\beta_3$ and $\alpha_v\beta_5$, which are overexpressed on many cancer cell types and are involved in cancer malignancy through promoting angiogenesis and metastasis. Desgrosellier, J. S.; Cheresh, D. A., Nat. Rev. Cancer, 10 (1), 9-22 (2010). Dimers displaying A647 with and without RGD were formed through a three-step process (FIG. 5a). First, CPMV was labeled with A647 and/or RGD through a combination of NHS ester chemistry and copper (I)-catalyzed azide-alkyne cycloaddition. Particles were functionalized with dyes before labeling with RGD to ensure the extent of dye labeling was consistent for CPMV-A647 compared to CPMV-A647-RGD. UV/visible spectroscopy revealed that 20 dyes were attached per particle, agarose gel electrophoresis confirmed successful labeling of the particles with dyes and RGD, and densitometric analysis following SDS-PAGE resulted in an estimate of 20-30 RGD labels per particle. A low density of dyes and RGD allowed for the formation of symmetry-broken particles in the next step using the previously described Method 2, with similar yields as found for unmodified particles. Finally, the particles were linked together using the same homobifunctional maleimide PEG linkers as before to form dimers. The resulting library of dimers included homodimers of CPMV-A647 and CPMV-A647-RGD as well as heterodimers formed by linking CPMV-A647 to CPMV-RGD. TEM imaging was performed to confirm successful dimer formation, and the percentage of dimers was consistent with what was found previously.

Flow cytometry was performed using HeLa cells, a cervical cancer cell line expressing $\alpha_v\beta_3$ and $\alpha_v\beta_5$ (Werner et al., Innate Immun., 18 (1), 55-69 (2012)), to compare extent of cell uptake for the different formulations of single particles and dimers (FIG. 5b-c). The dimers were added in two different concentrations, one in which the CPMV concentration is the same across all formulations (1 dimer for every 2 single particles; denoted as 1:2) and one in which the CPMV concentration for the dimers was doubled (1 dimer for every 1 single particle; denoted as 1:1). This is particularly important for making comparisons with the CPMV-A647/RGD heterodimer since the dye concentration is half of the concentration for all the other formulations when the CPMV concentration is kept constant.

First of all, it was observed that addition of RGD even at low densities increased cell targeting 3-fold when comparing single particle formulations; this increased cell targeting is attributed to expression of $\alpha_v\beta_3$ and $\alpha_v\beta_5$, the molecular targets of RGD, on HeLa cells. Next, homodimers versus their single particle formulations were compared. For both CPMV-A647 and CPMV-A647-RGD, there was significantly more uptake observed for the dimers compared to their respective single particle components. In fact, uptake of the CPMV-A647-RGD homodimer (1:2) was more than double what was observed for CPMV-A647-RGD. Size, aspect ratio, and ligand density likely play a role in these observations. The optimal nanocarrier size for endocytosis is a compromise between having the particles large enough to reduce the bending energy required for wrapping the cell membrane around the particles while also maintaining a size of particles small enough to reduce the receptor diffusion and membrane wrapping times; through competition between these factors, 30-50 nm was found to be the optimal radius. Gao et al., Proc. Natl. Acad. Sci. U.S.A. 2005, 102 (27), 9469-9474; Jiang et al., Nat. Nanotechnol., 3 (3), 145-150 (2008) Considering that CPMV has a 15 nm radius, the dimers may have more favorable dimensions, hence resulting in the observed trend of greater uptake of the dimers. The results also indicate that aspect ratio can be used as a handle to increase cell targeting. Cell targeting was increased 2.5-fold for RGD-targeted homodimers with AR 2 versus single particles with AR 1 (normalized to the same number of dyes and RGD ligands; a normalization on a per cluster/particle basis yielded a 4.2-fold increase in cell uptake). This is consistent with a recent study that indicated synergistic enhancement in cell target affinity and specificity as a combined contribution of particle morphology and molecular recognition chemistry. Barua et al., Proc. Natl. Acad. Sci. U.S.A., 110 (9), 3270-3275 (2013) Further studies would lead to greater understanding of the optimal AR for cell uptake. An additional consideration that accounts for the even greater uptake observed for the CPMV-A647-RGD homodimer in particular is the higher multivalency of RGD displayed on the dimer, as multivalency enhances both affinity and internalization. Boturyn et al., J. Am. Chem. Soc., 126 (18), 5730-5739 (2004).

The behavior of the heterodimer was also investigated. It was observed that RGD displayed on the CPMV-A647/RGD heterodimer (1:1) does confer some additional cell uptake when assessed against CPMV-A647 single particles and homodimers. Although this increase was statistically significant, uptake of the CPMV-A647/RGD heterodimer did not reach the same levels as that of CPMV-A647-RGD single particles, where A647 and RGD were both displayed on the same particle. It is likely that CPMV-A647-RGD presents the RGD ligands more efficiently; the spatial distribution of RGD ligands on only one particle of the heterodimer reduces the probability of ligand interaction with its integrin as there is a dependence on the orientation of the particle with respect to the cell. The CPMV-A647-RGD homodimer outperformed the heterodimer to an even greater extent, with 6.5-7.8 times higher uptake. It has the further advantage of greater multivalency from displaying double the number of RGD ligands versus the heterodimer. Cells are typically 10-100 times larger than nanoparticles, so the cell surface tends to be relatively flat in comparison. The homodimer structure may therefore interact with a larger number of binding sites on the cell surface, thus increasing targeting sensitivity and specificity. In addition, as membrane wrapping occurs, the CPMV-A647-RGD homodimer presents more sites for attachment to induce internalization along with receptor clustering and diffusion. From these observations, it can be concluded that enhanced cancer cell targeting was achieved as a synergistic contribution of receptor targeting, spatial orientation of targeting molecules, and nanoparticle shape (dimer versus single particle).

Conclusion

In summary, the inventors have successfully engineered symmetry-broken CPMV, employed a collection of PEG polymers to link the particles together to form novel assemblies, and investigated the behaviors of multifunctional dimers in vitro. Although the dimer samples are not quite monodisperse, the inventors can nevertheless begin to see and separate out the effects of shape, size, and distribution of functional groups. With the particle composition of the assemblies remaining the same, one can be confident that observed effects are not confounded by other factors such as surface charge.

The work has established the strategy of combining nanoparticles using a polymer-mediated method that has the potential to create novel architectures not yet realized with either top-down or bottom-up synthesis. The constructions are not restricted to just the chains and clusters demonstrated here. There is great potential to extend this approach to create more sophisticated and complex 3D nanostructures through intelligent polymer design. By taking into consideration the flexibility of various polymers and the spacing between functional groups, the distance and orientation of particles can be precisely guided and well-ordered structures formed. Furthermore, the incorporation of degradable polymers would pave the way for the development of multistage drug delivery systems. This could be realized through the assembly of specialized, asymmetric nanoparticles into a heterostructure, in which components can be released with spatial and temporal control during different stages of disease progression and treatment schedules. Besides applications in medicine, such mesoscale, hierarchical assemblies are envisioned to find manifold applications in energy-relevant materials and nanoelectronics, photonics, and sensing applications.

Methods

Symmetry-breaking of CPMV. Method 1: CPMV was reacted overnight at room temperature with 1000 molar excess of N-succinimidyl S-acetylthioacetate (SATA, Pierce) with 10% (v/v) DMSO at a final concentration of 2 mg/mL in 0.1 M potassium phosphate (KP) buffer, pH 7.0. Purification was performed using 10 kDa molecular weight cut-off centrifugal filter units (Millipore). Deacetylation of CPMV-SATA was carried out at 2 mg/mL final concentration with 0.1 M hydroxylamine, 5 mM EDTA in KP buffer, pH 7.5. After 2 hours, buffer exchange was performed 3 times with KP buffer using 10 kDa centrifugal filters. 1 mL of CPMV-SH was then placed in a fritted syringe containing 250 mg of activated thiol Sepharose 4B resin (GE Healthcare) that was previously hydrated with 5×5 mL of KP buffer and allowed to bind overnight with agitation. Any unbound CPMV-SH was removed from the syringe and 4 mL of fresh 50 mM iodoacetic acid (IAA, Acros Organics) in KP buffer, pH 7.5 was added to passivate any unbound thiols. The syringe was left overnight with agitation. The syringe was subsequently washed with 5 mL of KP buffer then CPMV-scIAA-aSH removed from the syringe by incubation with 1.5 mL of 50 mM β-mercaptoethanol overnight. Finally, buffer exchange was performed 5 times with KP buffer using 10 kDa centrifugal filters.

Method 2: 250 mg of amine-functionalized CLEAR™-base resin (Peptides International) was hydrated in a fritted syringe with 5 mL of DMSO for 6 hours with agitation. The DMSO was then discarded and 1 molar equivalent of PEG NHS ester disulfide linker (Polypure™) in 2 mL DMSO added to the syringe and allowed to react for 20 minutes with mixing. Unbound linker was removed by quickly washing with 5×5 mL of 20% DMSO in KP buffer. 2 mg of CPMV in 1.5 mL of 20% DMSO in KP buffer was then added and allowed to bind overnight with agitation. Unbound CPMV was removed and the syringe washed with KP buffer. CPMV-aSH was released from the syringe with 1.5 mL of fresh 20 mM TCEP (EMD Biosciences) in KP buffer. The TCEP was removed with buffer exchange 5 times with KP buffer using 10 kDa centrifugal filters.

CPMV assembly. The symmetry-broken particles were linked together to form dimers using homobifunctional PEG maleimide linkers (MW 2,000), clusters up to tetramers were formed with four-arm PEG maleimide (MW 20,000), and up to octamers with eight-arm PEG maleimide (MW 40,000) (all from Nanocs). 10 molar excess of the bifunctional linker, ¼ molar excess of the four-arm linker, and ⅛ molar excesses of the eight-arm linker were used. Reactions were carried out in KP buffer containing 10% DMSO at 0.2 mg/mL final concentration CPMV. For clusters formed by avidin addition, reactions were performed in KP buffer at a final concentration of 0.75 mg/mL CPMV-sBio or CPMV-scIAA-sBio. 5 molar excess of avidin was added and aggregation of CPMV-sBio+avidin was visible within 30 minutes. The samples were imaged with TEM after two hours.

Quantification of thiols introduced. The following bioconjugation reactions were all performed at 2 mg/mL final concentration of CPMV in KP buffer containing 10% DMSO at room temperature overnight, with mixing. To determine the quantity of protected thiols introduced for CPMV-SATA, the interior cysteines were first blocked using 6000 molar excess of Oregon Green 488 (O488) maleimide (Invitrogen™). Then, after reaction with SATA, deacetylation, and purification, 3000 molar excess of Alexa Fluor 647 (A647) maleimide (Invitrogen™) was used to label the introduced thiol groups and UV/visible spectroscopy used to determine the number of thiol groups attached. To verify passivation with IAA, the thiols of CPMV-SH and CPMV-scIAA-aSH were functionalized using 1000 molar excess of maleimide-PEG2-biotin (Pierce). For evaluation of the number of thiols introduced in CPMV-aSH, 2000 molar excess of O488 maleimide was used and reactions with wild type CPMV and CPMV-aSH were carried out side-by-side.

Bioconjugation of multifunctional CPMV and dimers. The following reactions were purified using 10 kDa molecular weight cut-off centrifugal filter units. CPMV was labeled with Alexa Fluor 647 succinimidyl ester (Invitrogen∩) using a 1500 molar excess of A647 at a final concentration of 10% DMSO and 2 mg/mL CPMV in KP buffer at room temperature overnight. CPMV and CPMV-A647 were then functionalized with cyclo[Arg-Gly-Asp-D-Phe-Lys(Azide)] (RGD, Peptides International) through a two-step reaction by first introducing an alkyne handle using same reaction conditions as for A647 except with 2000 molar excess of propargyl-NHS ester (Click Chemistry Tools), followed by copper-catalyzed azide-alkyne cycloaddition to conjugate the azide-functionalized RGD. The reaction was carried out for 2 hours at room temperature in KP buffer at a concentration of 1 mg/mL CPMV using a molar excess of 1500 RGD, aminoguanidine (20 mM in final solution), $CuSO_4$ (2 mM) with tris-(benzyltriazolylmethyl)amine (THPTA) (10 mM), and L-ascorbic acid (20 mM). Method 2 described above was used for symmetry breaking of the resulting CPMV-A647, CPMV-RGD, and CPMV-A647-RGD particles. CPMV-A647 and CPMV-A647-RGD homodimers were formed using the procedure outlined for CPMV dimers. For the CPMV-A647/RGD heterodimer, 1000 molar excess of the bifunctional linker was used to completely saturate the thiols of CPMV-A647-aSH. After 1 hour, the excess linkers were removed and CPMV-RGD-aSH added. All reactions were carried out in KP buffer containing 10% DMSO at 0.2 mg/mL final concentration CPMV.

UV/visible spectroscopy. Virus concentration was determined by UV/visible spectroscopy ($\varepsilon 260$ nm=8.1 $mg^{-1}$ mL $cm^{-1}$), the concentration of A647 labels using the fluorophore specific extinction coefficient at 651 nm ($\varepsilon$=265,000 $M^{-1}$ $cm^{-1}$ for maleimide and $\varepsilon$=270,000 $M^{-1}$ $cm^{-1}$ for NHS ester), and the concentration of O488 labels using its extinction coefficient at 491 nm ($\varepsilon$=81,000 $M^{-1}$ $cm^{-1}$).

Transmission electron microscopy. Carbon-coated copper TEM grids (Electron Microscopy Sciences) were placed over 20 μL drops of particles diluted to 0.1 mg/mL in DI water. Particles were allowed to adsorb for 5 minutes, the grid briefly rinsed with DI water, then negatively stained with 2% (w/v) uranyl acetate for 1 minute. Samples were imaged using a Zeiss Libra® 200FE transmission electron microscope operated at 200 kV.

Immunogold staining. CPMV-sBio and CPMV-scIAA-sBio samples were diluted to 0.05 mg/mL in KP buffer. TEM grids were placed over 20 μL drops of the particles and particles were allowed to adsorb for 20 minutes, after which the grids were rinsed briefly with KP buffer. Blocking was performed for 30 minutes with 1% (w/v) BSA (Pierce) and 0.1% (v/v) Tween 20 in KP buffer. After equilibration for 5 minutes with 0.1% BSA and 0.1% Tween 20 in KP buffer, the grids were incubated for 1 hour with 20 μL of undiluted 5 nm gold-labeled goat anti-biotin antibody (KPL). The grids were then washed 4 times over 20 minutes with KP buffer with 0.01% Tween, 2 times over 5 minutes with KP buffer, then finally 3 times over 10 minutes with DI water. After washing, the grids were stained with 2% uranyl acetate for 1 minute.

Gel electrophoresis. Native particles were analyzed by electrophoretic separation for 1 hour at 100 V on 1.2% (w/v) agarose gels containing EtBr in 1x TBE running buffer. Denaturing 4-12% NuPAGE gels (Invitrogen™) run at 200 V for 50 minutes in 1x MOPS running buffer (Invitrogen™) were used to analyze attachment to individual coat proteins. The denaturing gel was stained with GelCode Blue Stain Reagent (Pierce). The gels were then photographed using an AlphaImager® (Biosciences) imaging system.

Flow cytometry. HeLa cells (ATCC) were grown in minimal essential medium (MEM) supplemented with 10% (v/v) heat inactivated fetal bovine serum (FBS), 1% (v/v) L-glutamine, and 1% (v/v) penicillin-streptomycin (all from Gibco) at 37° C. in 5% $CO_2$. The cells were added to an untreated 96-well v-bottom plate at a density of 500,000 cells/200 μL MEM/well. Particles were added in triplicates at a concentration of 100,000 (for 1:2) or 200,000 (for 1:1) CPMV/cell and incubated for 1 hour at 37° C. and 5% $CO_2$. Cells were then washed twice by centrifuging the cells at 500 g for 4 minutes, gently removing the supernatant, and resuspending the cells in FACS buffer (0.1 mL 0.5 M EDTA, 0.5 mL FBS, and 1.25 mL 1 M HEPES, pH 7.0 in 50 mL $Ca^{2+}$ and $Mg^{2+}$ free PBS). The cells were fixed with 2% (v/v) paraformaldehyde in FACS buffer for 10 minutes at room temperature then washed twice again. BD LSR II flow cytometer was used for analysis, with a total of 10,000 events per sample collected. Data were analyzed using FlowJo software (Tree Star).

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. A plant virus particle multimer, the plant virus particle multimer produced by preparing a plurality of asymmetrically functionalized plant virus particles bearing one or more functional groups that are disposed asymmetrically and contacting the asymmetrically functionalized plant virus particles with a first linker molecule that reacts with the functional groups to form a plant virus particle multimer comprising a plurality of asymmetrically functionalized plant virus particles connected by the linker molecule, wherein the one or more asymmetrically disposed functional groups inhibit additional cluster formation and aggregation of the plant virus particles, wherein the plurality of asymmetrically functionalized plant virus particles are prepared by a method comprising the step of attaching a plurality of plant virus particles to a support surface to allow for asymmetrical functionalization of the plant virus particles and releasing the asymmetrically functionalized plant virus particles from the support surface to provide a plurality of unbound asymmetrically functionalized plant virus particles, and wherein the step of preparing a plurality of asymmetrically functionalized plant virus particles is performed at about physiological pH.

2. The plant virus particle multimer of claim 1, wherein the plant virus particles included in the multimer are icosahedral plant virus particles.

3. The plant virus particle multimer of claim 1, wherein the multimer is a dimer.

4. The plant virus particle multimer of claim 3, wherein the multimer is a heterodimer comprising a first and a second asymmetrically functionalized plant virus, wherein the first asymmetrically functionalized plant virus includes a targeting molecule bound to the surface and the second asymmetrically functionalized plant virus includes an imaging agent bound to the surface.

5. The plant virus particle multimer of claim 3, wherein the multimer is a homodimer comprising a first and a second asymmetrically functionalized plant virus, wherein both the first asymmetrically functionalized plant virus and the second asymmetrically functionalized plant virus include a targeting molecule and an imaging agent bound to the surface.

6. The plant virus particle multimer of claim 1, wherein the plant virus particle multimer further comprises an imaging agent.

7. The plant virus particle multimer of claim 1, wherein the plant virus particle multimer further comprises an anti-tumor agent.

8. The plant virus particle multimer of claim 1, wherein the plant virus particles included in the multimer are cow pea mosaic virus (CMPV) particles.

9. A method of delivering a cargo molecule to a cell, comprising contacting the cell with a plant virus particle multimer loaded with the cargo molecule, the plant virus particle multimer produced by preparing a plurality of asymmetrically functionalized virus particles bearing one or more functional groups that are disposed asymmetrically and contacting the asymmetrically functionalized plant virus particles with a first linker molecule that reacts with the functional groups to form a plant virus particle multimer comprising a plurality of asymmetrically functionalized plant virus particles connected by the linker molecule, wherein the one or more asymmetrically disposed functional groups inhibit additional cluster formation and aggregation of the plant virus particles, wherein the plurality of asymmetrically functionalized plant virus particles are prepared by a method comprising the step of attaching a plurality of plant virus particles to a support surface to allow for asymmetrical functionalization of the plant virus particles and releasing the asymmetrically functionalized plant virus particles from the support surface to provide a plurality of unbound asymmetrically functionalized plant virus particles, and wherein the step of preparing a plurality of asymmetrically functionalized plant virus particles is performed at about physiological pH.

10. The method of claim 9, wherein the multimer is a dimer.

11. The method of claim 10, wherein the multimer is a heterodimer comprising a first and a second asymmetrically functionalized plant virus, wherein the first asymmetrically functionalized plant virus includes a targeting molecule bound to the surface and the second asymmetrically functionalized plant virus includes an imaging agent bound to the surface.

12. The method of claim 10, wherein the multimer is a homodimer comprising a first and a second asymmetrically functionalized plant virus, wherein both the first asymmetrically functionalized plant virus and the second asymmetrically functionalized plant virus include a targeting molecule and an imaging agent bound to the surface.

13. The method of claim 9, wherein the cell is a cancer cell.

14. The method of claim 9, wherein the cargo molecule is an imaging agent.

15. The method of claim 9, wherein the cargo molecule is an antitumor agent.

16. The method of claim 9, wherein the cell is in vivo.

17. The method of claim 9, wherein the plant virus particle multimer further comprises a cell penetrating peptide and/or a targeting molecule bound to the surface of the plant virus particle multimer.

18. The method of claim 9, wherein the plant virus particle multimer is provided as part of a pharmaceutical composition.

19. The method of claim 9, wherein the plant virus particles included in the multimer are cow pea mosaic virus (CMPV) particles.

* * * * *